United States Patent [19]

Iwamoto et al.

[11] Patent Number: 5,246,989
[45] Date of Patent: Sep. 21, 1993

[54] PHOTOCHROMIC COMPOUND, COMPOSITION AND USE THEREOF

[75] Inventors: Kayo Iwamoto; Takashi Tanaka, both of Shin-nanyo; Satoshi Imura, Tokuyama; Seiji Okazaki, Tokuyama; Shinsuke Tanaka, Tokuyama, all of Japan

[73] Assignee: Tokuyama Soda Kabishiki Kaisha, Tokuyama, Japan

[21] Appl. No.: 676,285

[22] Filed: Mar. 28, 1991

[30] Foreign Application Priority Data

Mar. 29, 1990 [JP] Japan .................................. 2-78637
Aug. 1, 1990 [JP] Japan .................................. 2-202516
Nov. 8, 1990 [JP] Japan .................................. 2-301183
Nov. 8, 1990 [JP] Japan .................................. 2-301184

[51] Int. Cl.$^5$ .................... C08K 5/34; C07D 265/34
[52] U.S. Cl. ............................... 524/89; 529/90; 529/99; 529/102; 529/104
[58] Field of Search ................. 524/89, 90; 544/102, 544/99, 104

[56] References Cited
FOREIGN PATENT DOCUMENTS
30487 7/1986 Japan .

Primary Examiner—Kriellion S. Morgan
Attorney, Agent, or Firm—Sherman and Shalloway

[57] ABSTRACT

A photochromic compound of the present invention is a spiroxazine compound represented by the following formula:

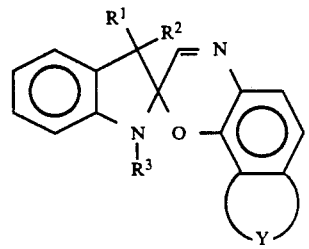

wherein $R^1$ to $R^3$ represent a monovalent organic group such as alkyl group, Y represents a fused heterocyclic aromatic hydrocarbon group or an unsaturated heterocyclic group if $R^1$ and $R^2$ are both methyl groups, and represents an aromatic hydrocarbon group or unsaturated heterocyclic group if $R^1$ and $R^2$ are other than the above mentioned. This compound shows an excellent photochromic characteristics even at high temperatures not less than ambient temperature.

26 Claims, 4 Drawing Sheets

PHOTOCHROMIC COMPOUND, COMPOSITION AND USE THEREOF

BACKGROUND OF THE INVENTION (1) Field of the Invention

The present invention relates to a novel compound having a photochromic action, a composition comprising this compound, and a use thereof. More particularly, the present invention relates to a novel compound which is colored from the colorless state under irradiation of an ultraviolet ray-containing light such as sunlight or a light of a mercury lamp, this change is reversible and the color fading speed is high, a composition comprising this novel compound and a use thereof.

(2) Description of the Related Art

The photochromism is the phenomenon which has attracted attention in these several years, and this phenomenon is a reversible phenomenon in which when a certain compound is irradiated with an ultraviolet ray-containing light such as sunlight or a light of a mercury lamp, the color of the compound is promptly changed and when the irradiation is stopped and the compound is placed in the dark place, the original color is manifested again. The compound having this property is called "photochromic compound", and various photochromic compounds have been synthesized. However, a special common structure is not found among these compounds.

The specification of Japanese Unexamined Patent publication No. 63-30487 discloses spiroxazine compounds represented by the following formula:

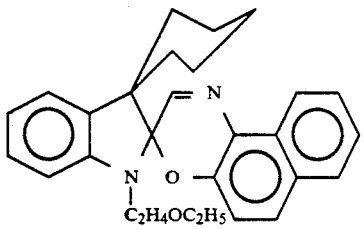

The compounds show photochromic characteristics in a solution or a polymer matrix. However, although the photochromic characteristics of the spiroxazine compounds is remarkable at temperatures not higher than 20° C., it is not excellent at temperatures close to the ambient temperature (20° to 30° C.), particularly higher than the ambient temperature.

Therefore, these compounds can not be used for a photochromic lens at relatively warm areas.

SUMMARY OF THE INVENTION

It is therefore a primary object of the present invention to provide a novel compound having a photochromic action.

Another object of the present invention is to provide a compound which shows the photochromic characteristics at relatively high temperatures not less than the ambient temperature.

Still another object of the present invention is to provide a photochromic compound having a practical utility.

A further object of the present invention is to provide a polymer composition comprising a photochromic compound.

A still further object of the present invention is to provide a photochromic lens having a practical utility.

As the result of research made by us, it was found that these objects could be attained by a photochromic compound described below.

More specifically, in accordance with the present invention, there is provided a spiroxazine compound represented by the following general formula (I):

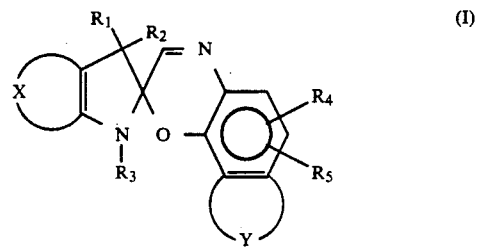

wherein $R_1$ and $R_2$ may be the same or different alkyl groups having 1 to 20 carbon atoms, or may together form a cycloalkyl ring, bicycloalkyl ring or a tricycloalkyl ring, $R_3$ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms, $R_4$ and $R_5$, which may be the same or different, represent a hydrogen atom, a halogen atom, an alkyl group having 1 to 10 carbon atoms, an aryl group having 6 to 10 carbon atoms, an aralkyl group having 7 to 14 carbon atoms, an alkoxy group having 1 to 10 carbon atoms, cyano group, a halogenoalkyl group having 1 to 4 carbon atoms, an amino group, a dialkylamino group having 2 to 20 carbon atoms, a 5- or 6-membered monocyclic heterocyclic group having one nitrogen atom or an alkoxycarbonyl group having 1 to 5 carbon atoms,

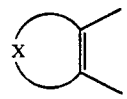

represents an aromatic hydrocarbon group which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenoalkyl group having 1 to 4 carbon atoms, a 5- or 6-membered monocyclic heterocyclic group, an aralkyl group having 7 to 14 carbon atoms or an alkoxy carbonyl group having 1 to 5 carbon atoms, or an unsaturated heterocyclic group which may be substituted with at least one constituent selected from the group consisting of a halogen atom and said groups, and

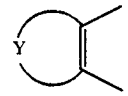

represents, when $R_1$ and $R_2$ are both methyl groups, a fused polycyclic aromatic hydrocarbon group which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms, or an unsaturated heterocyclic group which may be substituted with at least one constituent selected from the group consisting of a halogen atom and said groups, and represents, when $R_1$ and $R_2$ are other than the mentioned above, an aromatic hydrocarbon group which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms, or an unsaturated heterocyclic group which may be substituted with at least one constituent selected from the group consisting of a halogen atom and said groups.

The foregoing and other objects and features of the present invention will become more apparent from the following description.

DETAILED DESCRIPTION OF THE PREFERRED EMBODIMENTS

Figure 1:
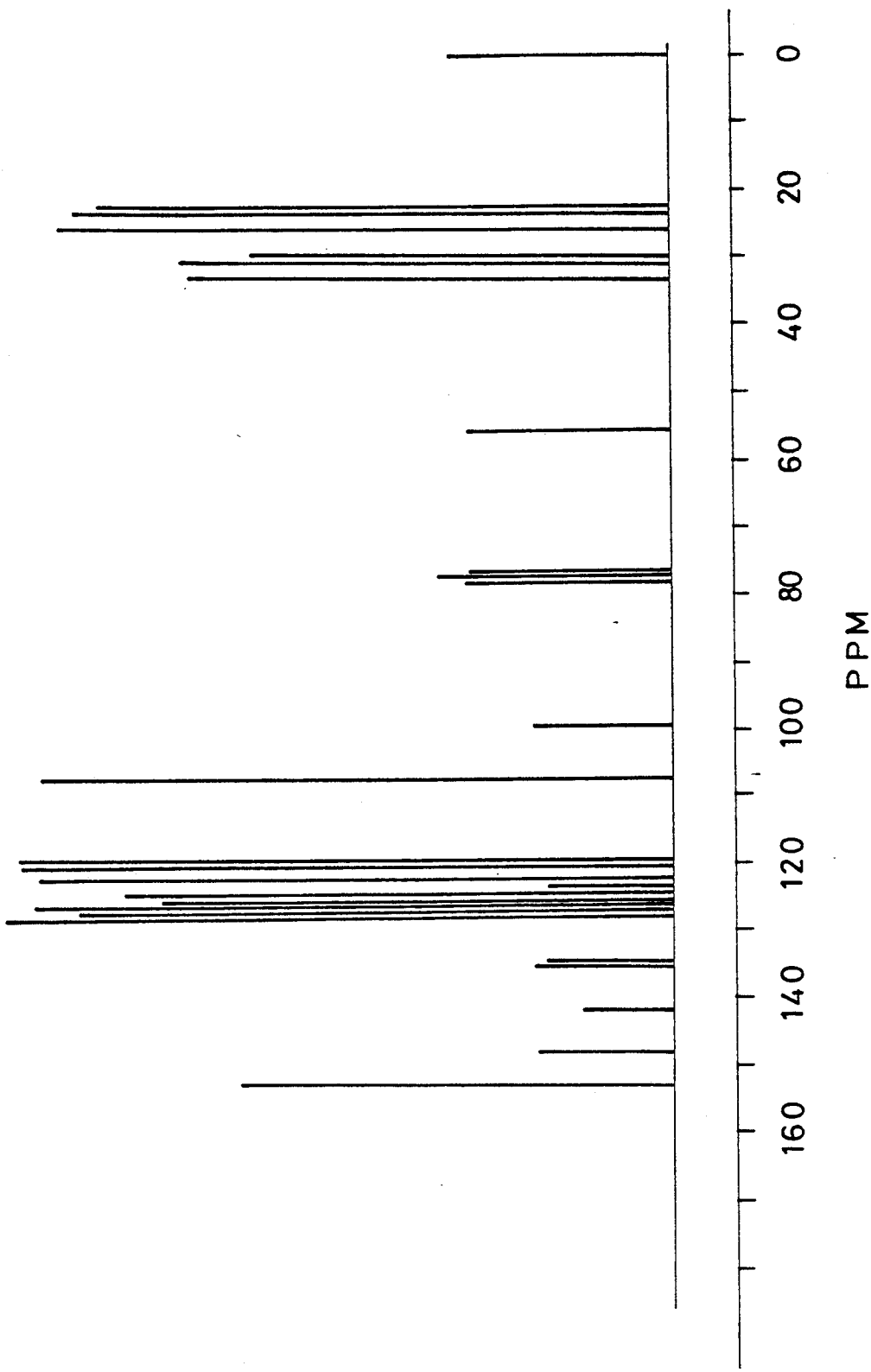
FIGS. 1, 2, 3 and 4 are 13C nuclear magnetic resonance spectrum charts of compounds obtained in Example 1, 26, 38 and 53, respectively.

In general formula (I), $R_1$ and $R_2$ which may be the same or different, are alkyl groups or may together form a ring.

Although not critical, it is desired that the alkyl group have 1 to 20, preferably 1 to 6 carbon atoms. The specific alkyl group includes, for example, a methyl group, an ethyl group, and an isopropyl group. When $R_1$ and $R_2$ together form a ring, a cycloalkyl group, a bicycloalkyl group and tricycloalkyl ring having 5 to 10 carbon atoms are generally preferable although not critical. More specifically, a divalent group derived from a cyclopentane ring, cyclohexane ring, a cycloheptane ring, a norbornane ring, an adamantane ring, a bicyclo (3.3.1) nonane ring and a bicyclo (2.2.1) hepthane ring is preferable.

In general formula (I), $R_3$ represents a hydrocarbon group, an alkoxycarbonylalkyl group or an cyanoalkyl group.

The hydrocarbon group is generally an alkyl group having 1 to 10 carbon atoms, preferably 1 to 4 carbon atoms, an aryl group having 6 to 10 carbon atoms, or an aralkyl group having 7 to 14 carbon atoms although not critical. Specific examples of the alkyl group include a methyl group, an ethyl group and an isopropyl group. The aryl group includes, for example, a phenyl group and a naphthyl group. The aralkyl group includes, for example, a benzyl group, a phenylethyl group, a phenylpropyl group, and a naphthylmethyl group. It is preferable that the alkoxy group of the alkoxycarbonylalkyl group has generally 1 to 10, preferably 1 to 4 carbon atoms although not critical. It is desired that the alkylene group of the alkoxycarbonylalkyl group has generally 1 to 10, preferably 1 to 4 carbon atoms although not critical. Specific examples of the alkoxycarbonylalkyl group include a methoxycarbonylmethyl group, a methoxycarbonylethyl group, a methoxycarbonylpropyl group, an ethyoxycarbonylmethyl group, an ethoxycarbonylethyl group, an ethoxycarbonylbutyl group, and a butoxycarbonylethyl group.

Although not critical, it is generally preferred that the cyanoalkyl group have 1 to 10, more preferably 1 to 4 carbon atoms. The specific examples of the cyanoalkyl group include a cyanomethyl group, a cyanoethyl group and a cyanopropyl group.

In the general formula (I), $R_4$ and $R_5$ represent a hydrogen atom, a halogen atom, a hydrocarbon group, an alkoxy group, a cyano group, a halogenoalkyl group, an amino group, a substituted amino group, and an alkoxycarbonyl group.

Although not critical, it is preferable that the hydrocarbon groups mentioned above be the hydrocarbon group described in relation to $R_3$.

Although not critical, it is desired that the alkoxy group has 1 to 10, preferably 1 to 4 carbon atoms. Specific examples of the alkoxy group includes a methoxy group, an ethoxy group, a propoxy group and a butoxy group. The halogen atom in the halogenoalkyl group is a fluorine atom, a chlorine atom or a bromine atom. The alkyl group having 1 to 4 carbon atoms is preferable. The specific examples of the halogenoalkyl group include a trifluoromethyl group, a trichloromethyl group and a tribromoethyl group.

The amino group or the substituted amino group is represented by the general formulae:

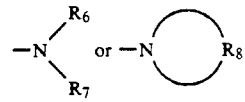

wherein $R_6$ and $R_7$, may be the same or different, and preferably represent a hydrogen atom, an alkyl group, an aralkyl group and an aryl group. When $R_4$ and $R_5$ are represented by the general formula

$R_8$ is preferably an alkylene group such as a tetramethylene group and a pentamethylene group; an oxyalkylene group such as

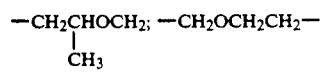

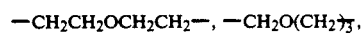

an thioalkylene group such as
—CH$_2$SCH$_2$CH$_2$CH—,   —CH$_2$S(CH$_2$)$_3$
—CH$_2$CH$_2$SCH$_2$CH$_2$—;
an thioalkylene group such as

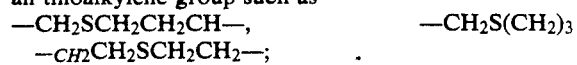

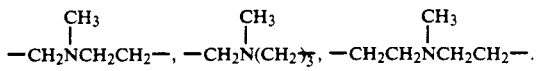

Although the alkoxycarbonyl group is not particularly critical, it is generally preferable that the number of the carbon atoms be 1 to 5, more preferably 1 to 3. Specific examples of the alkoxycarbonyl group include a methoxycarbonyl group, and an ethoxycarbonyl group.

In the general formula (I),

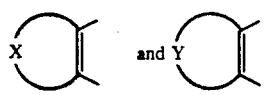

which may be the same or different, represent an aromatic hydrocarbon group which may be substituted or an unsaturated heterocyclic group which may be substituted. Specific examples of the aromatic hydrocarbon group include a divalent group derived from a ring having 6 to 18 carbon atoms constituting one benzene ring or 2 to 4 fused rings of a benzene ring, such as a benzene ring, a naphthalene ring, a phenanthrene ring and an anthracene ring. The aromatic hydrocarbon group may have at most 5, preferably up to 3 substituents. Examples of the substituent include halogen atoms such as fluorine, chlorine and bromine; a hydroxyl group; a cyano group; a nitro group; alkyl groups having 1 to 20 carbon atoms such as methyl group, an ethyl group, a propyl group and a butyl group; alkoxy groups having 1 to 20 carbon atoms such as a methoxy group, an ethoxy group, a propoxy group and a butoxy group; aryl groups having 6 to 10 carbon atoms such as a phenyl group, a tolyl group and naphthyl group; alkylamino groups having 1 to 4 carbon atoms such as a methylamino group and an ethylamino group; dialkylamino groups having 2 to 8 carbon atoms such as a dimethylamino group and a diethylamino group; halogenoalkyl groups having 1 to 4 carbon atoms such as trifluoromethyl group; 5- or 6-membered monocyclic heterocyclic groups having one or two of sulfur, oxygen and nitrogen atoms, such as a thienyl group, a furyl group, a pyrroyl group and a pyridyl group; aralkyl groups having 7 to 14 carbon atoms such as a benzyl group and a phenylethyl group; and alkoxycarbonyl groups having 1 to 5 carbon atoms such as a methoxycarbonyl group and an ethoxycarbonyl group.

The unsaturated heterocyclic groups which may have substituents and represented by

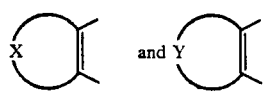

in the general formula (I) include a divalent group derived from a 5- or 6-membered heterocyclic ring containing oxygen, sulfur and nitrogen atoms or a heterocyclic ring which is formed by fusion of a benzene ring to the 5- or 6-membered heterocyclic ring mentioned above. Specific examples of the unsaturated heterocyclic group includes a divalent heterocyclic group derived from nitrogen-containing heterocyclic rings such as a pyridine ring, a quinoline ring, a pyrrol ring and an indole ring, oxygen-containing heterocyclic rings such as a furan ring and a benzofuran ring; sulfur-containing heterocyclic rings such as a thiophene ring and a benzothiophene ring.

The above mentioned substituents of the aromatic hydrocarbon group are adopted as the substitute of the unsaturated heterocyclic group without any particular limitation.

In the present invention, preferred compound includes the following two compound groups depending upon the kind of the groups represented by $R_1$, $R_2$ and

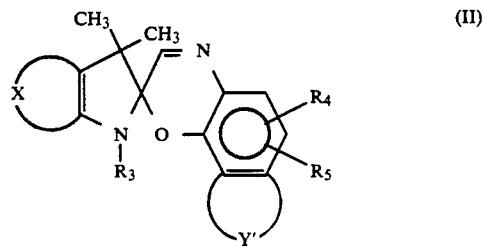

in the general formula (I).

The first compound group is represented by the general formula (II):

$R_3$ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms, $R_4$ and $R_5$, which may be the same or different, represent a hydrogen atom, a halogen atom, an alkyl group having 1 to 10 carbon atoms, an aryl group having 6 to 10 carbon atoms, an aralkyl group having 7 to 14 carbon atoms, an alkoxy group having 1 to 10 carbon atoms, a cyano group, a halogenoalkyl group having 1 to 4 carbon atoms, an amino group, a dialkylamino group having 2 to 20 carbon atoms, a 5- or 6-membered monocyclic heterocyclic group having one nitrogen atom or an alkoxycarbonyl group having 1 to 5 carbon atoms,

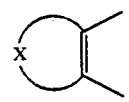

represents a group selected from the group consisting of an aromatic hydrocarbon group and an unsaturated heterocyclic group which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenoalkyl group having 1 to 4 carbon atoms, a 5- or 6-membered monocyclic heterocyclic group, an aralkyl group having 7 to 14 carbon atoms or an alkoxycarbonyl group having 1 to 5 carbon atoms, and

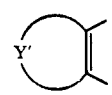

represents a group selected from the group consisting a fused polycyclic aromatic hydrocarbon group and an unsaturated heterocyclic group which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms.

In the compound represented by general formula (II) in which $R_1$ and $R_2$ in the general formula (I) are both methyl groups

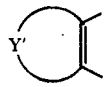

is a fused polycyclic aromatic hydrocarbon group or an unsaturated heterocyclic group which may have substituents. When

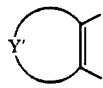

is other than either of the above mentioned groups, an excellent photochromic characteristics is not obtained at high temperatures.

The fused polycyclic aromatic hydrocarbon group represented by

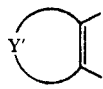

in the general formula (II) is a divalent group derived form a fused ring comprising more than one benzene ring. Among them, a divalent group derived from a fused ring comprising 2 to 4 benzene rings of a naphthalene ring, a phenanthrene ring or an anthracene ring is specially preferable.

The unsaturated heterocyclic group represented by

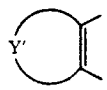

in the general formula (II) may be a group similar to the unsaturated heterocyclic group, which is described in relation to

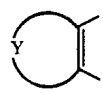

in the general formula (I).

The substituents of the fused polycyclic aromatic hydrocarbon group and the unsaturated heterocyclic group may be groups similar to the substituents which are described in relation to

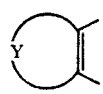

in the general formula (I).

Among the unsaturated heterocyclic groups represented by

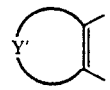

in the general formula (II), the divalent group derived from the pyridine ring may be a group represented as:

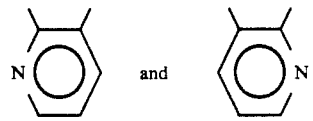

or a group represented as:

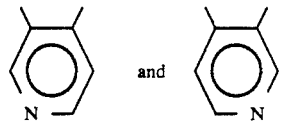

The latter group has a tendency to show higher coloration density.

In the present invention, it is preferable that in the general formula (II)

is an unsaturated heterocyclic group which may have substituents and a divalent group derived from a pyridine ring in view of the photochromic characteristics at relatively high temperatures.

In the present invention, the other preferred compound group is represented by the following formula:

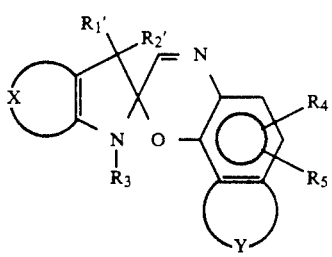

(III)

wherein $R_1'$ and $R_2'$ may be the same or different alkyl groups having 1 to 20 carbon atoms, or may together form a cycloalkyl ring, a bicycloalkyl ring or a tricycloalkyl ring, with the proviso that when $R_1'$ and $R_2'$ are both alkyl groups, at least one is an alkyl group having more than one carbon atom, $R_3$ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms, $R_4$ and $R_5$, which may be the same or different, represent a hydrogen atom, a halogen atom, an alkyl group having 1 to 10 carbon atoms, an aryl group having 6 to 10 carbon atoms, an aralkyl group having 7 to 14 carbon atoms, an alkoxy group having 1 to 10 carbon atoms, a cyano group, a halogenoalkyl group having 1 to 4 carbon atoms, an amino group, a dialkylamino group having 2 to 20 carbon atoms, a 5- or 6-membered monocyclic heterocyclic group having one nitrogen atom or an alkoxycarbonyl group having 1 to 5 carbon atoms,

represents a group selected from the group consisting of an aromatic hydrocarbon group and an unsaturated heterocyclic group which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenoalkyl group having 1 to 4 carbon atoms, a 5- or 6-membered monocyclic heterocyclic group, an aralkyl group having 7 to 14 carbon atoms or an alkoxycarbonyl group having 1 to 5 carbon atoms, and

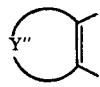

represents a group selected from the group consisting an aromatic hydrocarbon group and an unsaturated heterocyclic group which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms.

It is essential for the compounds to show an excellent coloration density at high temperatures that only one of $R_1'$ and $R_2'$ in the general formula (III) be an alkyl group having one or more carbon atoms and the other be an alkyl group having more than one carbon atoms or they together form a ring.

The aromatic hydrocarbon group, the unsaturated heterocyclic ring and the substituent of these groups represented by

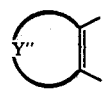

in the general formula (III) may be a group similar group described in relation to

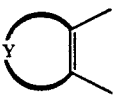

in the general formula (I).

Among the unsaturated heterocyclic groups, the group derived from the pyridine ring may be a group represented by

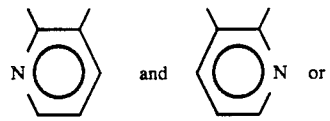

a group represented by

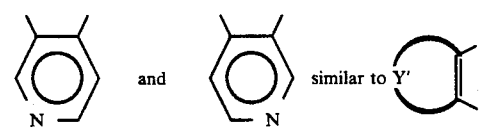

The latter has a tendency to show higher coloration density.

When

is a 5- or 6-membered heterocyclic ring especially a pyridine ring and $R_1'$ and $R_2'$ are alkyl groups or cycloalkyl groups, a higher coloration density can be obtained.

Specific examples of the compounds of the present invention will be exemplarily shown.

(1) 5'-fluoro-1'-methyldispiro[cyclohexane-1,3'-[3H]indole-2'(1'H),2''-[2H]naphth[1,2-b][1,4]oxazine]

(2) 5'-chloro-1'-methyldispiro[cyclopentane-1,3'-[3H]indole-2'(1'H),2''-[2H]naphth[1,2-b][1,4]oxazine]

(3) 5',7'-difluoro-1'-methyldispiro[cyclopentane-1,3'-[3H]indole-2'(1'H),2''-[2H]naphth[1,2-b][1,4]oxazine]

(4) 4'-methoxy-1'-methyldispiro[cyclopentane-1,3'-[3H]indole-2'(1'H),2''-[2H]naphth[1,2-b][1,4]oxazine]

(5) 1'-methyldispiro[cyclopentane-1,3'-[3H]indole-2'(1'H),2''-[2H]naphth[1,2-b][1,4]oxazine]

(6) 6'-dimethylamino-1'-methyldispiro[norbornane-2,3'[3H]indole-2'(1'H),2'''-[2H]naphth[1,2-b][1,4]oxazine]

(7) 1'-propyl-5'-trifluoromethyldispiro[tricyclo[3.3.1.1$^{3,7}$]decane-2,3'-[3H]indole-2'(1'H),2''-[2H]naphth[1,2-b][1,4]oxazine]

(8) 5'-dimethylamino-6''-bromo-1'-methoxycarbonylmethyldispiro[cycloheptane-1,3'-[3H]indole-2'(1'H),2'''-[2H]naphth[1,2-b][1,4]oxazine]

(9) 5'-methoxy-1'-phenyldispiro[cycloheptane-1,3'-[3H]indole-2'(1'H),2''-[2H]naphth[1,2-b][1,4]oxazine]

(10) 1'-methyl-5'-nitrodispiro[cycloheptane-1,3'-[3H]indole-2'(1'H),2''-[2H]naphth[1,2-b][1,4]oxazine]

(11) 6'-benzyl-1'-methyldispiro[cycloheptane-1,3'-[3H]indole-2'(1'H),2''-[2H]naphth[1,2-b][1,4]oxazine]

(12) 1,3-dihydro-1,3,3-trimethylspiro[3H-indole-2,2'-(2H)pyrido[2,3-h][1,4]benzoxazine]

(13) 9''-cyano-1'-(2-phenylethyl)dispiro[cyclohexane-1,2'-[3H]indole-2'(1'H),2''-[2H]pyrido[2,3-h][1,4] benzoxazine]

(14) 5'chloro-1'-methyl-6''-piperidinodispiro [tricyclo[3.3.1.1$^{3,7}$]decane-2,3'-[3H]indole-2'(1'H),2''-[2H]pyrido[2,3-h][1,4]benzoxazine]

(15) 1'-methoxycarbonylmethyl-6"-phenyldispiro[norbornane-2,3'-[3H]indole-2'(1'H),2"-[2H]pyrido[2,3-h][1,4]benzoxazine]

(16) 1,3-dihydro-5'-trifluoromethyl-1,3,3-trimethylspiro[2H-indole-2,2'-[2H]pyrido[2,3-h][1,4]benzoxazine]

(17) 1-cyanomethyl-1,3-dihydro-3,3-dimethyl-5-trifluoromethylspiro[2H-indole-2,2'-[2H]pyrido[2,3-h][1,4]benzoxazine]

(18) 1,3-dihydro-3,3-dimethyl-1-ethyl-6'-phenylspriro[2H-indole-2,2'-[2H]pyrido[2,3-h][1,4]benzoxazine]

(19) 1,3-dihydro-6'-pyrrolidino-1,3,3-trimethylspriro[2H-indole-2,2'-[2H]pyrido[2,3-h][1,4]benzoxazine]

(20) 6'-benzyl-9'-bromo-5-cyano-1,3-dihydro-1,3,3-trimethylspriro[2H-indole-2,2'-[2H]pyrido[2,3-h][1,4]benzoxazine]

(21) 1,3-dihydro-6-pyrrolidino-5'-trifluoromethyl-1,3,3-trimethylspriro[2H-indole-2,2'-[2H]pyrido[2,3-h][1,4]benzoxazine]

(22) 5'-amino-1,3-dihydro-1,3,3-trimethylspiro[2H-indole-2,2'-[2H]pyrido[2,3-h][1,4]benzoxazine]

(23) 1,3-dihydro-5'-methoxycarbonyl-1,3,3-trimethyl-5,6,7-tris-(trifluoromethyl)spiro[2H-indole-2,2'-[2H]pyrido[2,3-h][1,4]benzoxazine]

(24) 1,3-dihydro-1,3,3-trimethylspiro[2H-indole-2,2'-[2H]pyrido[3,4-h][1,4]benzoxazine]

(25) 1,3-dihydro-1,3,3-triethylspiro[2H-indole-2,2'[2H]pyrido[3,4-h][1,4]benzoxazine]

(26) 1,3-dihydro-5-fluoro-1,3,3-trimethylspiro[2H-indole-2,2'-[2H]pyrido[3,4-h][1,4]benzoxazine]

(27) 5-chloro-1,3-dihydro-1,3,3-trimethylspiro[2 H-indole-2,2'-[2H]pyrido[3,4-h][1,4]benzoxazine]

(28) 7'-bromo-1'-isopropylidispiro[cyclohexane-1,3'-[3H]indol-2'(1'H),2"-[2H]pyrido[3,4-h][1,4]benzoxazine]

(29) 1,3-dihydro-5-trifluoromethyl-1,3,3-trimethylspiro[2H-indole-2,2'-[2H]pyrido[3,4-h][1,4]benzoxazine]

(30) 6'-dimethylamino-1'-ethyl-6"-methoxydispiro[cyclopentane-1,3'-[3H]indole-2'(1'H),2"-[2H]pyrido[3,4-h][1,4]benzoxazine]

(31) 1'-benzyl-6"-dimethylamino-5'-phenyldispiro[cyclopentane-1,3'-[3H]indole-2'(1'H),2"-[2H]pyrido[3,4-h][1,4]benzoxazine]

(32) 1-methoxycarbonylmethyl-6'-cyano-1,3-dihydro-3,3-dimethylspiro[2H-indole-2,2'-[2H]pyrido[3,4-h][1,4]benzoxazine]

(33) 5'-chloro-1-cyanomethyl-1,3-dihydro-3,3-dimethylspiro[2H-indole-2,2'-[2H]pyrido[3,4-h][1,4]benzoxazine]

(34) 1,3-dihydro-3,3-dimethyl-1-(2-phenylethyl)-6'-pyrrolidinospiro[2H-indole-2,2'-[2H]pyrido[3,4-h][1,4]benzoxazine]

(35) 1'-dimethyldispiro[norbornane-2-3'-[3H]indole-2'(1'H),241 -[2H]pyrido[3,4-h][1,4]benzoxazine]

(36) 1,3-dihydro-6'methoxycarbonyl-1,3,3-trimethylspiro[2H-indole-2,2'-[2H]pyrido[3,4-h][1,4]benzoxazine]

(37) 6-cyano-1,3-dihydro-1,3,3-tirmethylspiro[2H-indole-2,2'-[2H]pyrido[4,3-h][1,4]benzoxazine]

(38) 1,3-dihydro-1,3,3-triethylspiro[2H-indole-2,2'[2H]pyrido[4,3-h][1,4]benzoxazine]

(39) 1,3-dihydro-5-fluoro-1,3,3-triethylspiro[2H-indole-2,2'[2H]pyrido[4,3-h][1,4]benzoxazine]

(40) 7-bromo-1,3-dihydro-1,3,3-triethylspiro[2H-indole-2,2'-[2H]pyrido[4,3-h][1,4]benzoxazine]

(41) 1'-methyldispiro[cyclohexane-1,3'-[3H]indole-2'(1'H),2"-[2H]pyrido[4,3-h][1,4]benzoxazine]

(42) 1'-isopropyldispiro[cyclopentane-1,3'-[3H]indole-2'(1'H),2"-[2H]pyrido[4,3-H][1,4]benzoxazine]

(43) 1-benzyl-5-chloro-3,3-diethyl-1,3-dihydro-5'-methylspiro[2H-indole-2,2'-[2H]pyrido[4,3-h][1,4]benzoxazine]

(44) 5'-chloro-3,3-diethyl-1,3-dihydro-6dimethylamino-1-methylspiro[2H-indole-2,2'-[2H]pyrido[4,3-h][1,4]benzoxazine]

(45) 1,3-dihydro-3,3-dipropyl-8'-methoxy-1-methylspiro[2H-indole-2,2'-[2H]pyrido[4,3-h][1,4]benzoxazine]

(46) 6"-methoxy-1'-methyldispiro[norbornane-2,3-[3H]indole-2'(1'H),2"-[2H]pyrido[4,3-h][1,4]benzoxazine]

(47) 1-methoxycarbonylmethyl-1,3-dihydro-3,3-dimethylspiro[2H-indole-2,2'-[2H]pyrido[4,3-h][1,4]benzoxazine]

(48) 1-methoxycarbonylmethyl-6'cyano-1,3-dihydro-3,3-dimethyl-5-phenylspiro[2H-indole-2,2'-[2H]pyrido[4,3-h][1,4]benzoxazine]

(49) 7'-amino-1cyanomethyl-1,3-dihydro-5-diethylamino-3-ethyl-3-methylspiro[2H-indole-2,2'-[2H]pyrido[4,3-h][1,4]benzoxazine]

(50) 1'-methyl-6"-pyrrolidinodispiro[cyclohexane-1,3'-[3H]indole-2'(1'H),2"-[2H]pyrido[4,3-h][1,4]benzoxazine]

(51) 1'-benzyl-5'-chloro-1,3-dihydro-3,3-dimethyl-6-dimethylamino-8'-methoxyspiro[2H-indole-2,2'[2H]pyrido [4,3-h][1,4]benzoxazine]

(52) 1,3-dihydro-6'methoxycarbonyl-1,3,3-trimethylspiro[2H-indole-2,2'-[2H]pyrido[4,3-h][1,4]benoxazine]

(53) 1,3-dihydro-1,3,3-trimethylspiro[2H-indole-2,2'[2H]pyrido[3,2-h][1,4]benoxazine]

(54) 1,3-dihydro-1,3,3-tripropylspiro[2H-indole-2,2'[2H]pyrido[3,2-h][1,4]benozazine]

(55) 1,3-dihydro-5-fluoro-1,3,3-tripropylspiro[2H-indole-2,2'-[2H]-pyrido[3,2-h][1,4]benzoxazine]

(56) 5-chloro-1,3-dihydro-1,3,3-tripropylspiro[2H-indole-2,2'[2H]-pyrido[3,2-h][1,4]benzoxazine]

(57) 7'-bromo-1'-t-butyldispiro[cyclohexane-1,3-[3H]indole-2'(1'H),2"-[2H]pyrido[3,2-h][1,4]benzoxazine]

(58) 1,3-dihydro-5-trifluoromethyl-1,3,3-trimethylspiro[2H-indole-2,2'-[2H]pyrido[3,2-h][1,4]benzoxazine]

(59) 6'-dimethylamino-1'-ethyl-6"-methoxydispiro[cyclohexane-1,3'-[3H]indole-2'(1'H),2"-[2H]pyrido[3,2-h][1,4]benzoxazine]

(60) 1'-benzyl-1,3-dihydro-3,3-dimethyl-6'-dimethylamino-5-phenylspiro[2H]indole-2,2'-[2H]pyrido[3,2-h][1,4]benzoxazine]

(61) 1-methoxycarbonylmethyl-6'-cyano-1,3-dihydro-3,3-dimethylspiro[2H]indole-2,2'-[2H]pyrido[3,2-h][1,4]benzoxazine]

(62) 5'-chloro-1-(2-cyanoethyl)-1,3-dihydro-3,3-dimethylspiro[2H-indole-2,2'-[2H]pyrido[3,2-h][1,4]benzoxazine]

(63) 1,3-dihydro-3,3-dimethyl-6'-pyrrolidino-1-(2-phenylethyl)spiro[2H-indole-2,2'-[2H]pyrido[3,2-h][1,4]benzoxazine]

(64) 1'-methyldispiro[norbornane-2,3'-[3H]indole-2'(1'H),2"-[2H]pyrido[3,2-h][1,4]benzoxazine]

(65) 1,3-dihydro-6'-ethoxycarbonyl-1,3,3-trimethylspiro[2H-indole-2,2'-[2H]pyrido[3,2-h][1,4]benzoxazine]

(66) 6-cyano-1,3-dihydro-1,3,3-trimethylspiro[2H-indole-2,2'-[2H]pyrido[3,2-h][1,4]benzoxazine]

(67) 1,3-dihydro-1,3,3-trimethylspiro[2H-indole-2,2'-[2H]anthara[1,2-b][1,4]oxazine]

(68) 1,3-dihydro-7'-methoxy-1,3,3-trimethylspiro[2H-indole-2,2'-[2H]anthara[1,2-b][1,4]oxazine]

(69) 1,3-dihydro-1,3,3-trimethylspiro[2H-indole-2,2'-[2H]([1H]pyrrolo)[6,7-b]naphth[1,2-b][1,4]oxazine]

(70) 1,3-dihydro-1,3,3-trimethylspiro[2H-indole-2,2'-[2H]([1H]pyrrolo)[2,3-h][1,4]benzoxazine]

(71) 1,3-dihydro-6'-methoxycarbonyl-1,3,3-trimethyl-spiro[2H-indole-2,2'-[2H]([1H]pyrrolo)[2,3-h][1,4]benzoxazine]

(72) 1,3-dihydro-1,3,3-trimethylspiro[2H-indole-2,2'-[2H]thieno[2,3-h][1,4]benzoxazine]

(73) 1'-methylspiro(cyclohexane-1,3'-[2H indole-2'(1H),2"-[2H]thieno[2,3-h][1,4]benzoxazine]

(74) 1,3-dihydro-1,3,3-trimethylspiro[2H-indole-2,2'-[2H]furane[2,3-h][1,4]benzoxazine]

The compound represented by the above-mentioned general formula (I) is a colorless or light yellow solid or viscous liquid at normal temperature under atmospheric pressure, and the compound can be identified, for example, by the following means (A) through (C).

(A) By measuring the proton nuclear magnetic resonance spectrum ($^1$H-NMR), the kind and number of protons present in the molecule can be known. Namely, a peak assigned to the aromatic proton appears in the vicinity of δ6.5 to 9 ppm and a peak assigned to the proton of the alkyl group in the vicinity of δ1.2 to 2.5 ppm, a peak due to the proton of the carbon bonded with the nitrogen atom of $R_3$ appears in the vicinity of δ2 to 4 ppm, a peak assigned to the proton of the carbon bonded to the carbonyl in the case where $R_4$ is a alkoxycarbonyl group appears in the vicinity of δ2.5 to 4 ppm and a peak assigned to the proton of the carbon bonded to the oxygen appears in the vicinity of δ3.5 to 4 ppm. By comparing the intensities of the peaks with one another, the numbers of protons of the respective binding groups can be known.

(B) The contents (% by weight) of carbon, hydrogen. nitrogen, sulfur and halogen can be determined by the elementary analysis. Furthermore, the content (% by weight) of oxygen can be calculated by subtracting the sum of the contents (% by weight) of the confirmed elements from 100. Accordingly, the composition of the product can be determined.

By measuring the $^{13}$C-nuclear magnetic resonance spectrum, the kind of the carbon present in the molecule can be known. A peak assigned to the primary and secondary carbons appears in the vicinity of δ20 to 50 ppm, a peak assigned to the carbon of the unsaturated hydrocarbon group or the unsaturated heterocyclic group appears in the vicinity of δ110 to 150 ppm, a peak assigned to the spiro carbon appears in the vicinity of 100 ppm and a peak assigned to the carbon of the carbonyl appears in the vicinity of δ170 ppm.

The process for preparing the compound represented by the general formula (I) according to the present invention is not particularly critical. Typical processes preferably adopted will now be described.

The process is carried out by reacting an azolium salt represented by the general formula (IV):

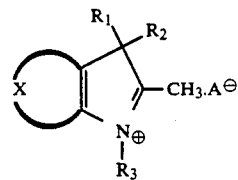

wherein $R_1$ and $R_2$ may be the same or different alkyl groups having 1 to 20 carbon atoms, or may together form a cycloalkyl ring, a bicycloalkyl ring or a tricycloalkyl ring, $R_3$ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms,

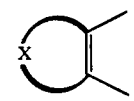

represents a group selected from the group consisting of an aromatic hydrocarbon group and an unsaturated heterocyclic group which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenoalkyl group having 1 to 4 carbon atoms, a 5- or 6-membered monocyclic heterocyclic group, an aralkyl group having 7 to 14 carbon atoms or an alkoxycarbonyl group having 1 to 5 carbon atoms.

A represents an anion with a nitroso compound represented by the general formula (V):

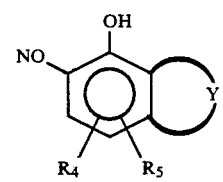

$R_4$ and $R_5$, which may be the same or different, represent a hydrogen atom, a halogen atom, an alkyl group having 1 to 10 carbon atoms, an aryl group having 6 to 10 carbon atoms, an aralkyl group having 7 to 14 carbon atoms, an alkoxy group having 1 to 10 carbon atoms, a cyano group, a halogenoalkyl group having 1 to 4 carbon atoms, an amino group, a dialkylamino group having 2 to 20 carbon atoms, a 5- or 6-membered monocyclic heterocyclic group having one nitrogen atom or an alkoxycarbonyl group having 1 to 5 carbon atoms, and

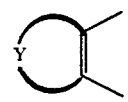

represents a group selected from the group consisting an aromatic hydrocarbon group and an unsaturated heterocyclic group which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms, with the proviso that when $R_1$ and $R_2$ are both methyl group, said aromatic hydrocarbon group is a fused polycyclic aromatic hydrocarbon group.

The reaction between the compound represented by the general formula (IV) with the compound represented by the general formula (V) is carried out in the following method. The reaction ratio between the two compounds can be selected in a broad range, however in general, the reaction ratio is selected in the range of from 1/10 to 10/1 (molar ratio). It is generally preferred that the reaction temperature be 0° to 200° C. A polar solvent such as methyl alcohol, ethyl alcohol, N-methylpyrrolidone, dimethylformamide, tetrahydrofuran is used as the reaction solvent. The reaction is carried out in the presence of a known base represented by amines including tertiary amine such as triethylamine and secondary amine such as diethylamine, piperidine, pyrrolidine, morpholine; and inorganic bases such as alkali metal hydroxides or alkali metal carbonates. It is preferable that the condensing agent be used in an amount of 0.1 to 10 moles per mole of the compound of the general formula (IV).

The spiroxazine compound represented by the formula (I) of the present invention is well soluble in ordinary organic solvents such as toluene, chloroform, teterahydrofuran. If the compound of general formula (I) is dissolved in such an organic solvent, the solution is generally colorless and transparent. When the solution is irradiated with sunlight or ultraviolet rays, the solution is promptly colored. If the solution is insulated from the light, the solution is promptly restored to the original colorless state. Thus, the compound of general formula (I) shows a good reversible photochromic action. This photochromic action of the compound of general formula (I) is also caused in a polymer solid matrix. The reversing speed is in the order of second. Any of polymers in which the spiroxazine compound of general formula (I) of the present invention is uniformly dispersed can be used as the polymer constituting the polymer matrix. Any of thermoplastic resins and thermosetting resins may be adopted as the polymer solid material.

The thermoplastic resins include, for example, polymethyl acrylate, polyethyl acrylate, polymethyl methacrylate, polyethyl methacrylate, polystyrene, polyacrylonitrile, polyvinyl alcohol, polyacrylamide, poly(2-hydroxyethylmethacrylate), polydimethylsiloxane, polycarbonate.

Dispersion of the compound represented by the general formula (I) of the present invention into a thermoplastic resin can be carried out by the synthesis of the thermoplastic, that is, the polymerization or melting and mixing the thermoplastic resin and the compound at temperature not less than a melting point of the thermoplastic resin.

The thermosetting resins includes the polymers of radical polymeric multifunctional monomers which include, for example, polyvalent acrylate and polyvalent methacrylate compounds such as ethylene glycol diacrylate, diethylane glycol dimethacrylate, ethylene glycol bisglycidyl methacrylate, bisphenol A dimethacrylate, 2,2-bis(4-methacryloyl oxyethoxy phenyl) propane, 2,2-bis(3,5-dibromo-4-methacryloyl oxyethoxy phenyl) propane; polyvalent allyl compounds such as diallyl phthalate, diallyl terephthalate, diallyl isophthalate, diallyl epoxy succinate, diallyl fumarate, diallyl chlorendate, diallyl hexaphthalate, diallyl carbonate, allyl diglycol carbonate, trimethylolpropane triallyl carbonate; polyvalent thioacrylate and polyvalent thiomethacrylate compounds such as 1,2-bis (methacryloylthio) ethane, bis(2-acryloyl thioethyl) ether, 1,4-bis(-methacryloylthiomethyl) benzene; and divinylbenzene. The thermosetting resins may also include, for example, copolymers of the radical polymeric multifunction monomers with radical polymeric monofunctional monomers including unsaturated carboxylic acids such as acrylic acid, methacrylic acid, maleic anhydride; acrylate and methacrylate compounds such as methyl acrylate, methyl methacrylate, benzyl methacrylate, phenyl methacrylate, 2-hydroxyethyl methacrylate; fumarate compounds such as diethyl fumarate, diphenyl fumarate; thioacrylate and thiomethacrylate compounds such as methyl thioacrylate, benzyl thioacrylate, benzyl thiomethacrylate; and vinyl compounds such as styrene, chlorostyrene, methylstyrene, vinylnaphthalene, bromostyrene. The thermosetting resins may further include addition copolymers of the above mentioned radical polymeric multifunctional monomers with polyvalent thiol compounds such as ethanedithiol, propanethiol, hexanodithiol, pentaerythritol, tetrakisthioglycolate, di(2-mercaptoethyl)ether; and addition copolymers of polyvalent isocyanate compounds such as diphenylethane diisocyanate, xylene diisocyanate, p-phenylene diisocyanate with polyvalent alcohol compounds such as ethylene glycol, trimethylol propane, pentaerythritol, bisphenol A or the above mentioned polyvalent thiol compounds.

Dispersion of the compound of the general formula (I) into the thermosetting resin may be generally carried out by mixing the starting monomers of the thermosetting resin with the compound of the general formula (I) and thereafter polymerizing them.

The mixing ratio of spiroxazine compound of the present invention to the polymer as mentioned above is not critical. However, in order to obtain an excellent coloration density and not to lower the solid state property of the polymer, it is preferred that the spiroxazine compound be used in an amount of 0.001 to 70 parts by weight per 100 parts by weight of the polymer.

Accordingly, the compound of the present invention can be widely used as the photochromic compound. For example, the compounds of the present invention can be used as various recording materials for example, various memory materials, copying materials printing photosensitive material, cathode ray tube recording materials, laser photosensitive materials and holographic photosensitive materials instead of the conventional silver salt photosensitive materials. Furthermore, the photochromic material comprising the compound of the present invention can be used as a photochromic lens material, an optical filter material, a display material, an actinometer material and a decorative material. For example, when the material is used for a photochromic lens, any method can be used without any particular limitation, so far as a uniform dimming performance is obtained. For example, there can be adopted in which a homogeneous dispersion of the compound of the present invention in a polymer film is sandwiched in a lens, and a method in which the compound of the present invention is dissolved in, for example, a silicone oil, the surface of a lens is impregnated with the solution at 150° to 200° C. over a period of 10 to 60 minutes and the impregnated surface is covered with a hardenable substance to form a photochromic lens. Furthermore, there can be considered a method in which the above-mentioned polymer film is coated on the surface of a lens and the surface is covered with a hardenable substance to form a photochromic lens.

The spiroxazine compound of the present invention shows the marked photochromic characteristic in a high-molecular solid matrix, of course, at temperatures in the vicinity of ambient temperature 20° to 30° C., even at temperatures (30° to 40°) higher than the ambient temperature.

The present invention will now be described in detail with reference to the following examples that by no means limit the scope of the invention.

EXAMPLE 1

2.01 g (0.0059 mol) of a compound represented by the following formula:

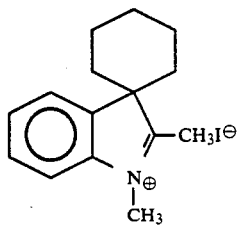

1.02 g (0.0059 mol) of a compound represented by the following formula:

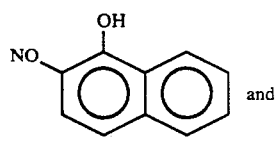

and 0.43 g (0.006 mol) of pyrrolidine were dissolved in 50 ml of ethyl alcohol and heated under the reflux over a period of 2 hours.

After the termination of the reaction, the solvent was removed. Then, the obtained liquid was purified by the chromatography on silica gel to obtain 400 mg of spiroxazine compound of the following formula:

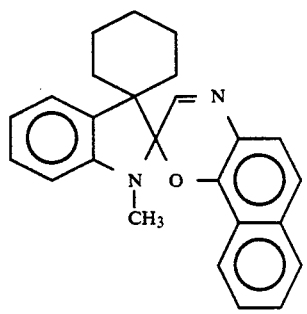

(1)

The elementary analysis values of the obtained compound were 81.35% for C, 6.60% for H, 7.62% for N, 4.43% for O, which were well in agreement with the theoretical values of $C_{25}H_{24}N_2O$, that is, 81.49% for C, 6.57% for H, 7.60% for N, and 4.34% for O. When the proton nuclear magnetic resonance spectrum was measured, it was found that peaks of 11H assigned to the proton of the naphthalene ring, the proton of the indoline ring and the proton of the oxazine ring appeared in the vicinity of $\delta 6.5$ to 8.0 ppm, a peak of 3H assigned to the proton of the bond

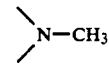

appeared in the vicinity of $\delta 2.8$ ppm and a broad peak of 10H assigned to the proton of the cyclohexane ring in the vicinity of $\delta 1.3$ to 2.0 ppm. When the $^{13}C$-nuclear magnetic resonance spectrum (FIG. 1) was measured, peaks assigned to the carbons, of the benzene ring of the indoline, naphthalene ring and oxazine rings appeared in the vicinity of $\delta 100$ to 160 ppm, peaks assigned to the spiro carbon appeared in the vicinity of $\delta 99$ ppm and 52 ppm and peaks assigned to the carbons of the cyclohexane group and methyl group appeared in the vicinity of $\delta 20$ to 35 ppm. From the foregoing results, it was confirmed that the isolated product was the compound represented by the above-mentioned structural formula (1).

EXAMPLE 2

2.10 g (0.0057 mol) of a compound represented by the following formula:

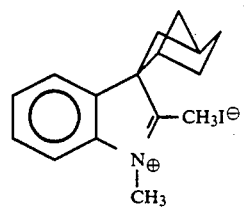

0.98 g (0.0057 mol) of a compound represented by the following formula:

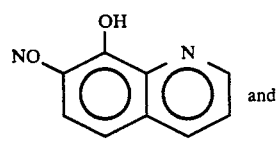

and 0.41 g (0.0057 mol) of pyrrolidine were dissolved in 50 ml of ethyl alcohol and heated under the reflux over a period of 2 hours.

After the termination of the reaction, the solvent was removed. Then, the obtained liquid was purified by the chromatography on silica gel to obtain 200 mg of spiroxazine compound of the following formula:

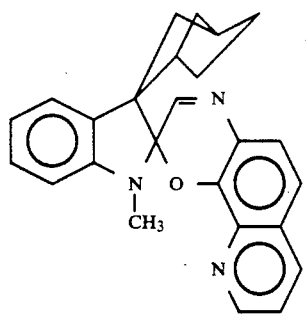
(2)

The elementary analysis values of the obtained compound were 78.66% for C, 6.09 for H, 11.05 for N, and 4.2% for O, which were well in agreement with the theoretical values of $C_{25}H_{23}N_3O$, that is, 78.71% for C, 6.08% for H, 11.02% for N, and 4.2% for O. When the proton nuclear magnetic resonance spectrum was measured, it was found that peaks of 10H assigned to the proton of the quinoline ring, the proton of the indoline ring, and the proton of the oxazine ring appeared in the vicinity of δ6.5 to 9 ppm, a peak of 3H assigned to the proton of the bond

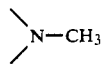

appeared in the vicinity of δ2.7 ppm and a broad peak of 10H attributed to the proton of norbornane ring appeared in the vicinity of δ1.3 to 2.5 ppm. When the $^{13}C$-nuclear magnetic resonance spectrum was measured, peaks assigned to the carbon of the benzene ring of the indoline, naphthalene ring and oxazine ring appeared in the vicinity of δ100 to 160 ppm, peaks assigned to the spiro carbon appeared in the vicinity of δ99 ppm and δ52 ppm and a peak assigned to the carbons of the norbornane group appeared in the vicinity of δ27 to 52 ppm. From the foregoing results, it was confirmed that the isolated product was the compound represented by the above-mentioned structural formula (2).

EXAMPLE 3 TO 25

The spiroxazine compounds represented in Table 1 were synthesized in the same method as described in Examples 1 and 2.

The structures of the obtained compounds were analyzed by the same structure-identification means as adopted in Example 1. It was confirmed that the obtained compounds were compounds represented by structural formula shown in Table 1.

The elementary analysis values of the compounds and the theoretical values calculated from the structural formulae of compounds are shown in Table 2.

TABLE 1

| Example No. | Starting Compounds | | Condensation Agent | Products | Yield (%) |
|---|---|---|---|---|---|
| 3 | [iminium salt with bicyclic/phenyl, N⊕(CH₃)(CH₃), I⊖] | [1-OH, 4-N(CH₃)₂, 3-NO naphthalene] | pyrrolidine (N-H) | [condensation product with N(CH₃)₂-naphthyl-O-N(CH₃)] | 15 |
| 4 | [iminium salt with adamantyl/CF₃-phenyl, N⊕(CH₃)(C₃H₇), I⊖] | [1-OH, 2-NO naphthalene] | pyrrolidine (N-H) | [condensation product with naphthyl-O-N(C₃H₇), CF₃-phenyl, adamantyl] | 13 |
| 5 | [iminium salt with C(C₂H₅)₂, hydroxypyridyl, N⊕(CH₃)(CH₃), I⊖] | [4-OH, 3-NO quinoline] | pyrrolidine (N-H) | [condensation product with quinolinyl-O-N(CH₃), C(C₂H₅)₂, hydroxypyridyl] | 13 |

TABLE 1-continued

| Example No. | Starting Compounds | | Condensation Agent | Products | Yield (%) |
|---|---|---|---|---|---|
| 6 | (structure) | (structure) | (structure) | (structure) | 15 |
| 7 | (structure) | (structure) | (structure) | (structure) | 18 |

TABLE 1-continued

| Example No. | Starting Compounds | | Condensation Agent | Products | Yield (%) |
|---|---|---|---|---|---|
| 8 | | | | | 10 |
| 9 | | | | | 8 |
| 10 | | | | | 12 |

TABLE 1-continued

| Example No. | Starting Compounds | Condensation Agent | Products | Yield (%) |
|---|---|---|---|---|
| 11 | | | | 6 |
| 12 | | | | 15 |

TABLE 1-continued

| Example No. | Starting Compounds | | Condensation Agent | Products | Yield (%) |
|---|---|---|---|---|---|
| 13 | | | | | 8 |
| 14 | | | | | 11 |

TABLE 1-continued

| Example No. | Starting Compounds | | Condensation Agent | Products | Yield (%) |
|---|---|---|---|---|---|
| 15 | | | | | 8 |
| 16 | | | | | 15 |
| 17 | | | | | 18 |

5,246,989
TABLE 1-continued
| Example No. | Starting Compounds | | Condensation Agent | Products | Yield (%) |
|---|---|---|---|---|---|
| 18 | 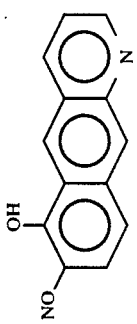 | 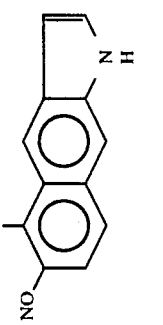 | 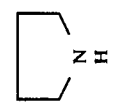 | 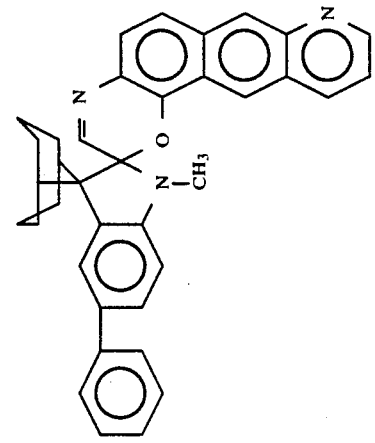 | 6 |
| 19 | 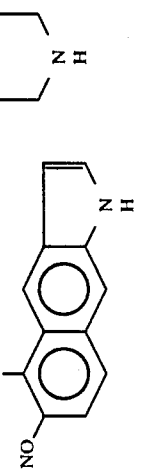 | | | | 11 |

TABLE 1-continued

| Example No. | Starting Compounds | | Condensation Agent | Products | Yield (%) |
|---|---|---|---|---|---|
| 20 | (structure) | (structure) | (pyrrolidine) | (structure) | 8 |
| 21 | (structure) | (structure) | (pyrrolidine) | (structure) | 10 |
| 22 | (structure) | (structure) | (pyrrolidine) | (structure) | 7 |

TABLE 1-continued

| Example No. | Starting Compounds | Condensation Agent | Products | Yield (%) |
|---|---|---|---|---|
| 23 | [adamantyl-substituted iodide salt with N⊕—C₄H₉, CH₃, I⊖, and C₂H₅-phenyl substituents] | [4-hydroxy-5-amino-6-nitrobenzofuran derivative] | [pyrrolidine, N–H] | [condensation product with NH₂, O, furan, N=, C₄H₉, adamantyl, and C₂H₅-phenyl groups] | 7 |
| 24 | [adamantyl-substituted bromide salt with N⊕—CH₂COOCH₃, CH₃, Br⊖, and Cl-phenyl substituents] | [3-hydroxy-2-nitro-7-bromoanthracene derivative] | [pyrrolidine, N–H] | [condensation product with anthracene, Br, OCH₂COOCH₃, N=, adamantyl, and Cl-phenyl groups] | 6 |

TABLE 1-continued
| Example No. | Starting Compounds | Condensation Agent | Products | Yield (%) |
|---|---|---|---|---|
| 25 | 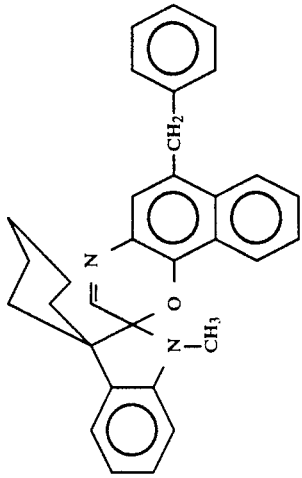 | 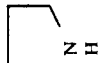 | 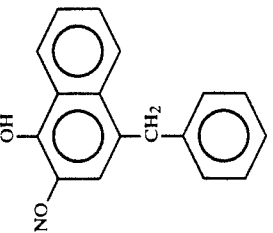 | 6 |

TABLE 2

| No. | Elementary Analysis Values (%) | | | | | Theoretical Values | | | | |
|---|---|---|---|---|---|---|---|---|---|---|
| | C | H | N | O | others | C | H | N | O | others |
| 3 | 79.33 | 6.96 | 9.91 | 3.80 | | 79.4 | 6.90 | 9.92 | 3.78 | |
| 4 | 80.26 | 6.55 | 5.88 | 3.36 | F: 3.95 | 80.31 | 6.53 | 5.85 | 3.34 | F: 3.97 |
| 5 | 70.55 | 5.85 | 15.00 | 8.60 | | 70.57 | 5.92 | 14.96 | 8.55 | |
| 6 | 76.60 | 6.57 | 9.60 | 7.23 | | 76.51 | 6.65 | 9.56 | 7.28 | |
| 7 | 79.32 | 5.88 | 11.50 | 3.30 | | 79.31 | 5.82 | 11.56 | 3.30 | |
| 8 | 79.97 | 5.65 | 6.70 | 7.68 | | 79.98 | 5.75 | 6.66 | 7.61 | |
| 9 | 73.47 | 6.56 | 10.40 | 2.99 | Cl: 6.58 | 73.52 | 6.54 | 10.39 | 2.97 | Cl: 6.58 |
| 10 | 72.41 | 5.90 | 11.64 | 3.31 | S: 6.74 | 72.47 | 5.87 | 11.66 | 3.33 | S: 6.67 |
| 11 | 63.57 | 5.53 | 7.70 | 8.70 | Br: 14.50 | 63.51 | 5.51 | 7.66 | 8.75 | Br: 14.57 |
| 12 | 75.28 | 6.68 | 9.69 | 8.35 | | 75.24 | 6.67 | 9.75 | 8.35 | |
| 13 | 76.57 | 6.11 | 9.33 | 7.99 | | 76.49 | 6.08 | 9.39 | 8.04 | |
| 14 | 63.87 | 4.23 | 9.20 | 13.30 | F: 9.40 | 64.79 | 4.18 | 9.30 | 13.28 | F: 9.46 |
| 15 | 77.96 | 5.71 | 7.62 | 2.90 | S: 5.81 | 78.09 | 5.64 | 7.59 | 2.89 | F: 5.79 |
| 16 | 80.55 | 5.90 | 6.30 | 7.25 | | 80.69 | 5.87 | 6.27 | 7.17 | |
| 17 | 74.01 | 5.53 | 16.64 | 3.82 | | 74.09 | 5.50 | 16.62 | 3.80 | |
| 18 | 82.96 | 6.24 | 7.80 | 3.00 | | 82.96 | 6.21 | 7.84 | 2.99 | |
| 19 | 76.82 | 6.27 | 9.63 | 7.28 | | 76.86 | 6.22 | 9.60 | 7.31 | |
| 20 | 68.23 | 6.00 | 13.91 | 11.86 | | 68.30 | 5.98 | 13.86 | 11.87 | |
| 21 | 72.68 | 5.63 | 10.11 | 11.58 | | 72.62 | 5.61 | 10.16 | 11.61 | |
| 22 | 74.72 | 7.18 | 6.72 | 3.74 | S: 7.64 | 74.60 | 7.22 | 6.69 | 3.82 | S: 7.66 |
| 23 | 76.40 | 7.32 | 9.26 | 7.02 | | 76.45 | 7.30 | 9.22 | 7.02 | |
| 24 | 65.57 | 4.74 | 4.33 | 7.44 | Cl: 5.50 Br: 12.42 | 65.48 | 4.71 | 4.36 | 7.48 | Cl: 5.52 Br: 12.45 |
| 25 | 83.79 | 6.57 | 6.14 | 3.50 | | 83.81 | 6.59 | 6.11 | 3.49 | |

EXAMPLE 26

2 g (0.0058 mol) of a compound represented by the following formula:

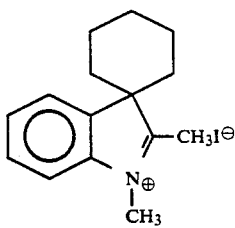

1.0 g (0.0058 mol) of a compound represented by the following formula:

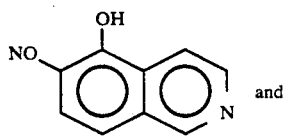

and 0.45 g (0.0063 mol) of pyrrolidine were dissolved in 50 ml of ethyl alcohol and heated under the reflux over a period of 2 hours.

After the termination of the reaction, the solvent was removed. Then, the obtained liquid was purified by the chromatography on silica gel to obtain 400 mg of spiroxane compound of the following formula:

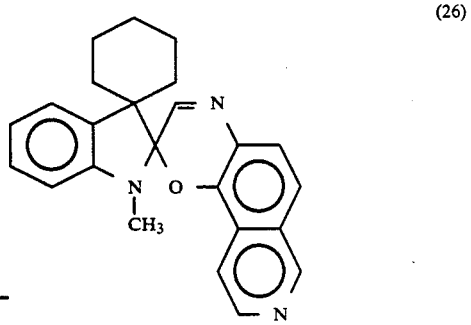

(26)

Figure 2:
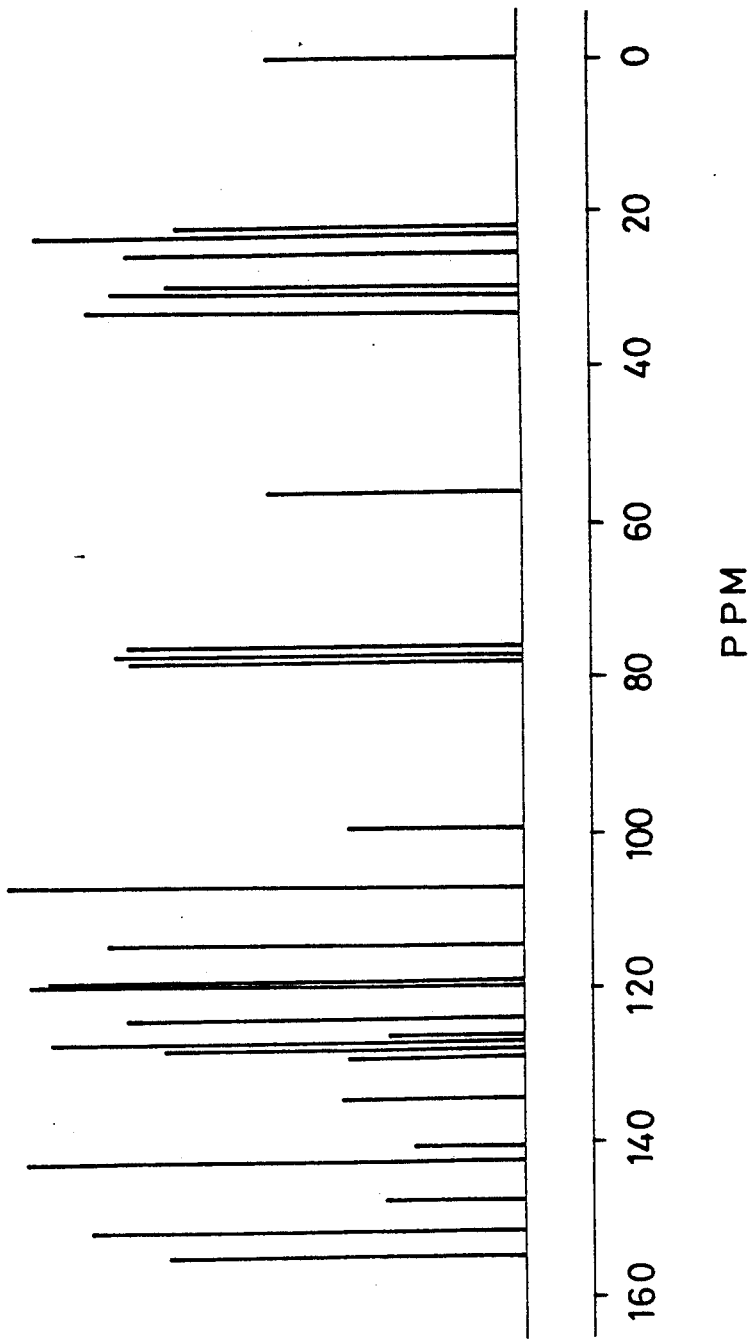

The elementary analysis values of the obtained compound were 77.92% for C, 6.34% for H, 11.48% for N, and 4.26% for O, which were well in agreement with the theoretical values of $C_{24}H_{20}N_3O$, that is, 78.02% for C, 6.27% for H, 11.37% for N, and 4.33% for O. When the proton nuclear magnetic resonance spectrum was measured, it was found that peaks of 10H assigned to the proton of the isoquinoline ring, the proton of the indoline ring, and the proton of the oxazine ring appeared in the vicinity of δ6.5 to 9.0 ppm, a peak of 3H assigned to the proton of the bond $$\begin{matrix}\diagdown\\ \diagup\end{matrix}N-CH_3$$

appeared in the vicinity of δ2.8 ppm, a peak of H assigned to the proton of the methyl group appeared in the vicinity of δ1.5 ppm, and a broad peak of 10H assigned to the proton of the cyclohexane ring in the vicinity of δ1.3 to 2.1 ppm. When the $^{13}C$-nuclear magnetic resonance spectrum (FIG. 2) was measured, peaks assigned to the carbon of the benzene ring of the indoline, isoquinoline ring and oxazine ring appeared in the vicinity of 100 to 160 ppm, peaks assigned to the spiro carbon appeared in the vicinity of δ99 ppm and δ52 ppm and peaks of assigned to the carbons of the methyl and methylene groups appeared in the vicinity of δ20 to 50 ppm. From the foregoing results, it was confirmed that the isolated product was the compound represented by the above-mentioned structural formula (26).

EXAMPLES 27 TO 37

The spiroxazine compounds represented in Table 3 were synthesized in the same method as described in Example 26.

The structures of the obtained compounds were analyzed by the same structure-identification means as adopted in Example 26. It was confirmed that the obtained compounds were compounds represented by structural formula shown in Table 3.

The elementary analysis values of the compounds and the theoretical values calculated from the structural formulae of compounds are shown in Table 4.

TABLE 3

| Example No. | Starting Compounds | | Condensation Agent | Products | Yield (%) |
|---|---|---|---|---|---|
| 27 | (cyclohexyl-phenyl with 2,4-diF, enamine N⊕(CH₃)(CH₃) CH₃I⊖) | 8-hydroxyisoquinoline | pyrrolidine | corresponding condensation product | 7 |
| 28 | (cyclopentyl-phenyl with 4-Cl, enamine N⊕(CH₃)(CH(CH₃)₂) CH₃I⊖) | 8-hydroxy-7-methylisoquinoline | piperidine | corresponding condensation product | 8 |
| 29 | (cycloheptyl-phenyl with 4-Br, enamine N⊕(CH₃)(CH(CH₃)₂) CH₃I⊖) | 8-hydroxy-1,3-dimethylisoquinoline | morpholine | corresponding condensation product | 4 |

TABLE 3-continued

| Example No. | Starting Compounds | | Condensation Agent | Products | Yield (%) |
|---|---|---|---|---|---|
| 30 | | | $(C_2H_5)_3N$ | | 12 |
| 31 | | | $(C_2H_5)_2NH$ | | 3 |
| 32 | | | | | 5 |

TABLE 3-continued

| Example No. | Starting Compounds | Condensation Agent | Products | Yield (%) |
|---|---|---|---|---|
| 33 | | Na₂CO₃ | | 3 |
| 34 | | NaOH | | 4 |
| 35 | | (pyrrolidine) | | 8 |

TABLE 3-continued

| Example No. | Starting Compounds | Condensation Agent | Products | Yield (%) |
|---|---|---|---|---|
| 36 | | | | 3 |
| 37 | | | | 4 |

TABLE 4

| Example No. | Elementary Analysis Value (%) | | | | | Theoretical Values (%) | | | | |
|---|---|---|---|---|---|---|---|---|---|---|
| | C | H | N | O | others | C | H | N | O | others |
| 27 | 71.00 | 5.34 | 10.28 | 3.93 | F: 9.45 | 71.09 | 5.22 | 10.36 | 3.95 | F: 9.37 |
| 28 | 72.18 | 6.10 | 9.65 | 3.59 | Cl: 8.38 | 72.29 | 6.07 | 9.73 | 3.70 | Cl: 8.21 |
| 29 | 67.03 | 6.35 | 7.99 | 3.03 | Br: 15.60 | 67.18 | 6.22 | 8.10 | 3.09 | Br: 15.41 |
| 30 | 75.32 | 5.69 | 6.89 | 2.57 | F: 9.53 | 75.35 | 5.66 | 6.94 | 2.64 | F: 9.41 |
| 31 | 77.75 | 6.05 | 7.50 | 8.70 | | 77.81 | 5.99 | 7.56 | 8.64 | |
| 32 | 71.38 | 6.42 | 9.98 | 5.75 | Cl: 6.47 | 71.40 | 6.35 | 10.09 | 5.76 | Cl: 6.39 |
| 33 | 67.65 | 5.74 | 7.85 | 12.01 | Cl: 6.75 | 67.73 | 5.68 | 7.90 | 12.03 | Cl: 6.66 |
| 34 | 75.13 | 5.08 | 10.22 | 2.96 | Cl: 6.61 | 75.20 | 5.01 | 10.32 | 2.95 | Cl: 6.53 |
| 35 | 57.18 | 4.53 | 8.83 | 7.64 | Br: 12.73 F: 9.09 | 57.24 | 4.48 | 8.90 | 7.63 | Br: 12.69 F: 9.05 |
| 36 | 59.98 | 5.91 | 15.25 | 2.91 | S: 5.95 | 70.05 | 5.88 | 15.32 | 2.92 | S: 5.84 |
| 37 | 74.52 | 6.15 | 11.37 | 7.96 | | 74.61 | 6.10 | 11.45 | 7.85 | |

EXAMPLE 38

2 g (0.0067 mol) of a compound represented by the following formula:

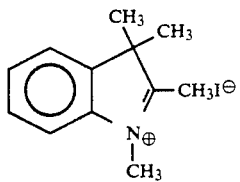

1.2 g (0.0067 mol) of a compound represented by the following formula:

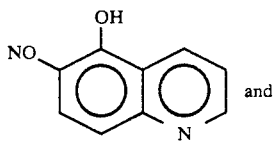

0.5 g (0.007 mol) of pyrrolidine were dissolved in 50 ml of ethyl alcohol and heated under the reflux over a period of 2 hours.

After the termination of the reaction, the solvent was removed. Then, the obtained liquid was purified by the chromatography on silica gel to obtain 300 mg of spiroxane compound of the following formula:

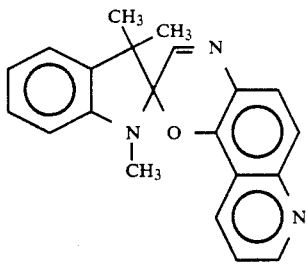

(38)

Figure 3:
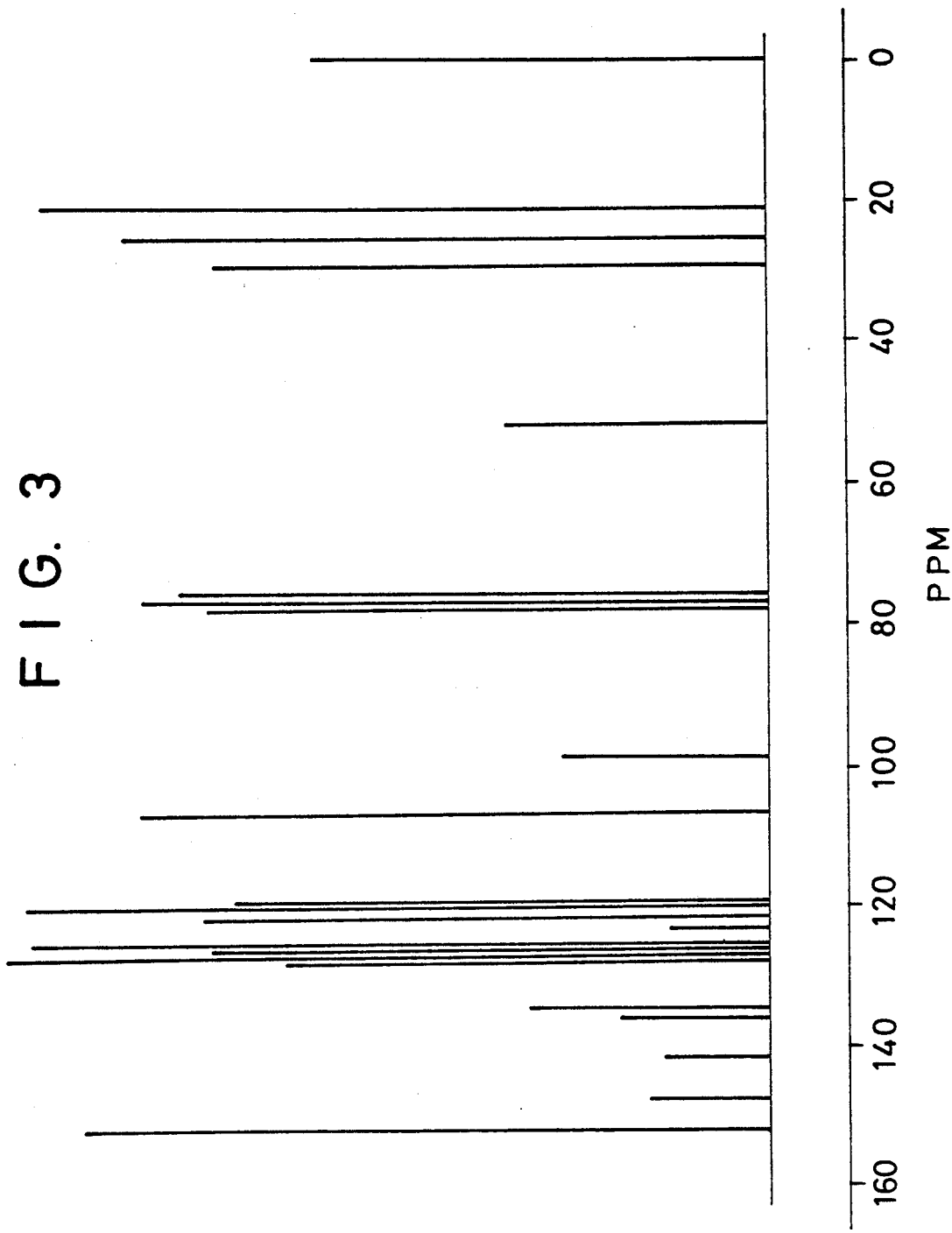

The elementary analysis values of the obtained compound were 76.61% for C, 5.78% for H, 12.70% for N, and 4.91% for O, which were well in agreement with the theoretical values of $C_{21}H_{19}N_3O$, that is, 76.57% for C, 5.81% for H, 12.76% for N, and 4.86% for O. When the proton nuclear magnetic resonance spectrum was measured, it was found that peaks of 10H assigned to the proton of the quinoline ring, the proton of the indoline ring, and the proton of the oxazine ring appeared in the vicinity of δ6.5 to 9.0 ppm, a peak of 3H assigned to the proton of the bond $$\diagdown N{-}CH_3 \diagup$$

appeared in the vicinity of δ2.8 ppm, a peak of 6H assigned to the proton of the methyl group appeared in the vicinity of δ1.5 ppm. When the $^{13}C$-nuclear magnetic resonance spectrum (FIG. 3) was measured, peaks assigned to the carbon of the benzene ring of the indoline, quinoline ring and oxazine ring appeared in the vicinity of δ100 to 160 ppm, peaks assigned to the spiro carbon appeared in the vicinity of δ99 ppm and 52 ppm and a peak assigned to the carbons of the methyl group appeared in the vicinity of δ20 ppm. From the foregoing results, it was confirmed that the isolated product was the compound represented by the above-mentioned structural formula (38).

EXAMPLE 39

2.0 g (0.0053 mol) of a compound represented by the following formula:

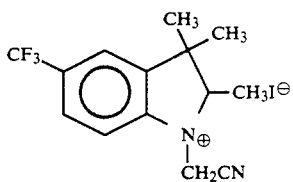

1.1 g (0.0053 mol) of a compound represented by the following formula:

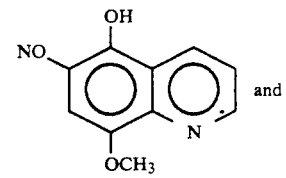

0.37 g (0.0053 mol) of pyrrolidine were dissolved in 50 ml of ethyl alcohol and heated under the reflux over a period of 2 hours.

After the termination of the reaction, the solvent was removed. Then, the obtained liquid was purified by the chromatography on silica gel to obtain 250 mg of spiroxazine compound of the following formula:

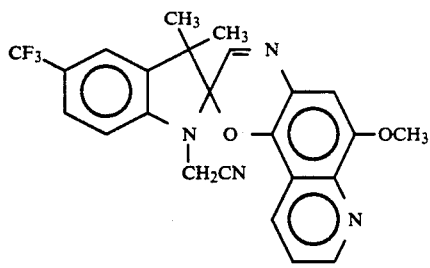 (39)

The elementary analysis values of the obtained compound were 64.00% for C, 4.20% for H, 12.36% for N, 7.06% for O, and 12.38% for F which were well in agreement with the theoretical values of $C_{24}H_{19}N_4O_2F_3$, that is, 63.7% for C, 4.23% for H, 12.38% for N, 7.07% for O and 12.6% for F. When the proton nuclear magnetic resonance spectrum was measured, it was found that peaks of 8H assigned to the proton of the quinoline ring, the proton of the indoline ring, and the proton of the oxazine ring appeared in the vicinity of δ6.5 to 9 ppm, a peak of 2H assigned to the proton of the bond

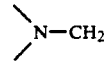

appeared in the vicinity of δ2.7 ppm, a peak of 6H assigned to the proton of the methyl group appeared in the vicinity of δ1.5 ppm and a peak assigned to the proton of the methoxy group appeared in the vicinity of δ3.8 ppm. From the foregoing results, it was confirmed that the isolated product is the compound represented by the above-mentioned structural formula 39.

EXAMPLES 40 TO 52

The spiroxazine compounds represented in Table 5 were synthesized in the same method as described in Examples 38 and 39.

The structures of the obtained compounds were analyzed by the same structure-identification means as adopted in Example 38. It was confirmed that the obtained compounds were compounds represented by structural formula shown in Table 5.

The elementary analysis values of the compounds and the theoretical values calculated from the structural formulae of compounds are shown in Table 6.

TABLE 5

| Example No. | Starting Compounds | | Condensation Agent | Products | Yield (%) |
|---|---|---|---|---|---|
| 40 | [structure] | [structure] | [structure] | [structure] | 5% |
| 41 | [structure] | [structure] | [structure] | [structure] | 7% |
| 42 | [structure] | [structure] | [structure] | [structure] | 8% |

TABLE 5-continued

| Example No. | Starting Compounds | | Condensation Agent | Products | Yield (%) |
|---|---|---|---|---|---|
| 43 | | | | | 10% |
| 44 | | | | | 12% |
| 45 | | | | | 9% |

TABLE 5-continued

| Example No. | Starting Compounds | Condensation Agent | Products | Yield (%) |
|---|---|---|---|---|
| 46 | | | | 7% |
| 47 | | | | 11% |
| 48 | | | | 5% |

TABLE 5-continued

| Example No. | Starting Compounds | | Condensation Agent | Products | Yield (%) |
|---|---|---|---|---|---|
| 49 | | | | | 8% |
| 50 | | | | | 12% |
| 51 | | | | | 15% |
| 52 | | | | | 7% |

TABLE 6

| | Elementary Analysis Values (%) | | | | | Theoretical Values (%) | | | | |
|---|---|---|---|---|---|---|---|---|---|---|
| | C | H | N | O | others | C | H | N | O | others |
| 40 | 57.15 | 3.60 | 4.80 | 8.12 | Br: 26.33 | 56.69 | 3.57 | 4.72 | 8.09 | Br: 26.94 |
| 41 | 71.19 | 4.35 | 9.81 | 7.30 | S: 7.35 | 71.38 | 4.38 | 9.60 | 7.31 | S: 7.33 |
| 42 | 71.86 | 4.40 | 10.76 | 9.28 | F: 3.70 | 71.80 | 4.47 | 10.8 | 9.26 | F: 3.66 |
| 43 | 82.44 | 5.86 | 8.40 | 3.30 | — | 82.4 | 5.90 | 8.48 | 3.23 | — |
| 44 | 71.05 | 6.40 | 13.35 | 9.20 | — | 71.11 | 6.35 | 13.37 | 9.17 | — |
| 45 | 72.64 | 4.82 | 12.14 | 10.40 | — | 72.71 | 4.80 | 12.11 | 10.38 | — |
| 46 | 72.32 | 5.51 | 14.10 | 8.07 | — | 72.34 | 5.57 | 14.06 | 8.03 | — |
| 47 | 77.73 | 5.90 | 13.30 | 3.07 | — | 77.69 | 5.94 | 13.32 | 3.04 | — |
| 48 | 63.15 | 4.10 | 10.90 | 6.20 | Br: 15.65 | 63.17 | 4.12 | 10.91 | 6.23 | Br: 15.57 |
| 49 | 66.93 | 5.43 | 12.04 | 3.40 | F: 12.20 | 66.94 | 5.40 | 12.01 | 3.43 | F: 12.22 |
| 50 | 68.76 | 4.79 | 13.85 | 6.30 | S: 6.30 | 68.76 | 4.78 | 13.82 | 6.32 | S: 6.33 |
| 51 | 52.84 | 3.10 | 7.12 | 8.14 | F: 28.80 | 52.80 | 3.07 | 7.11 | 8.12 | F: 28.91 |
| 52 | 71.25 | 5.51 | 10.79 | 12.45 | — | 71.30 | 5.46 | 10.85 | 12.39 | — |

EXAMPLE 53

2 g (0.0066 mol) of a compound represented by the following formula:

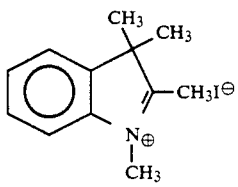

1.15 g (0.0066 mol) of a compound represented by the following formula:

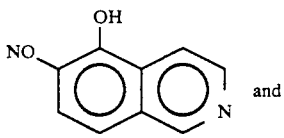

and 0.50 g (0.0070 mol) of pyrrolidine were dissolved in 50 ml of ethyl alcohol and heated under the reflux over a period of 2 hours.

After the termination of the reaction, the solvent was removed. Then, the obtained liquid was purified by the chromatography on silica gel to obtain 400 mg of spiroxazine compound of the following formula:

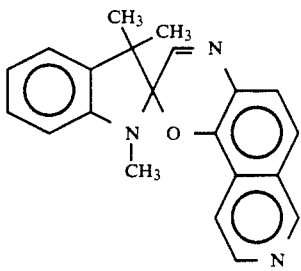

(53)

The elementary analysis values of the obtained compound were 76.52% for C, 5.93% for H, 12.68% for N and 4.87% for O, which were well in agreement with the theoretical values of $C_{21}H_{19}N_3O$, that is, 76.57% for C, 5.81% for H, 12.75% for N, and 4.86% for O. When the proton nuclear magnetic resonance spectrum was measured, it was found that peaks of 10H assigned to the proton of the isoquinoline ring, the proton of the indoline ring, and the proton of the oxazine ring appeared in the vicinity of δ6.5 to 9.0 ppm, a peak of 3H assigned to the proton of the bond

Figure 4:
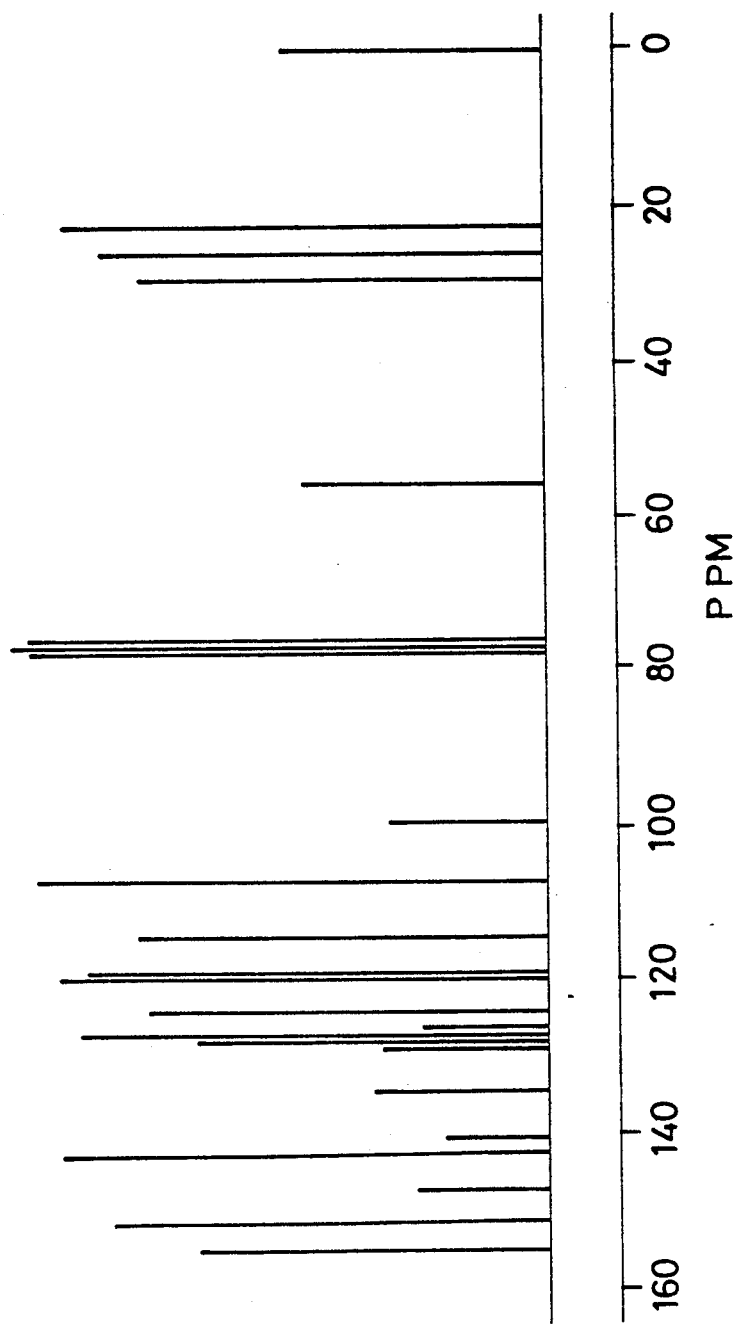

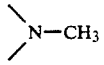

appeared in the vicinity of δ2.8 ppm, a peak of H ass to the proton of the methyl group appeared in the vicinity of δ1.5 ppm. When the $^{13}C$-nuclear magnetic resonance spectrum (FIG. 4) was measured, peaks assigned to the carbon of the benzene ring of the indoline, naphthalene ring and oxazine ring appeared in the vicinity of δ100 to 160 ppm, peaks assigned to the spiro carbon appeared in the vicinity of δ99 ppm and 52 ppm and peaks assigned to the carbon of the methyl group appeared in the vicinity of δ20 ppm. From the foregoing results, it was confirmed that the isolated product was the compound represented by the above-mentioned structural formula (53).

EXAMPLES 54 TO 64

The spiroxazine compounds represented in Table 7 were synthesized in the same method as described in Example 53.

The structures of the obtained compounds were analyzed by the same structure-identification means as adopted in Example 53. It was confirmed that the obtained compounds were compounds represented by structural formula shown in Table 7.

The elementary analysis values of the compounds and the theoretical values calculated from the structural formulae of compounds are shown in Table 8.

TABLE 7

| Example No. | Starting Compounds | | Condensation Agent | Products | Yield (%) |
|---|---|---|---|---|---|
| 54 | [structure] | [structure] | [structure] | [structure] | 7 |
| 55 | [structure] | [structure] | [structure] | [structure] | 8 |
| 56 | [structure] | [structure] | [structure] | [structure] | 4 |

TABLE 7-continued
| Example No. | Starting Compounds | | Condensation Agent | Products | Yield (%) |
|---|---|---|---|---|---|
| 57 | 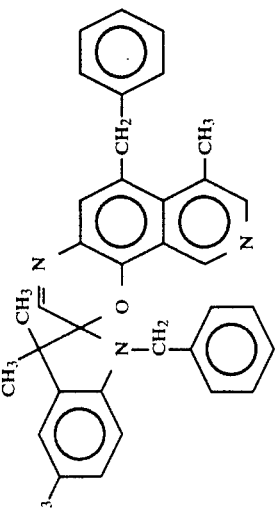 | 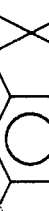 | (C$_2$H$_5$)$_3$N | 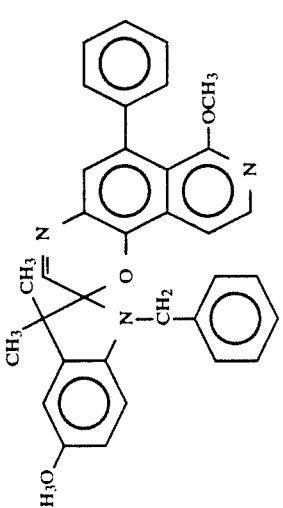 | 12 |
| 58 | 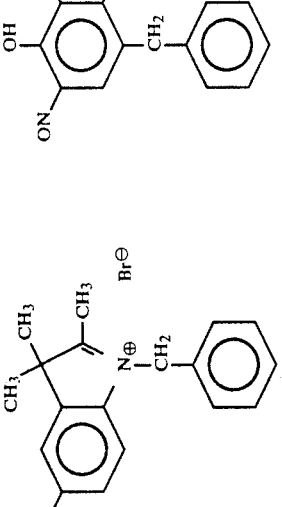 | 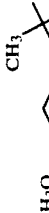 | (C$_2$H$_5$)$_2$NH | 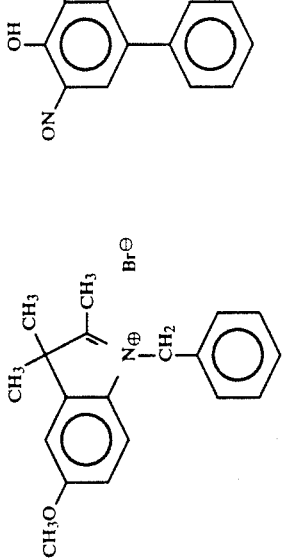 | 8 |
| 59 | 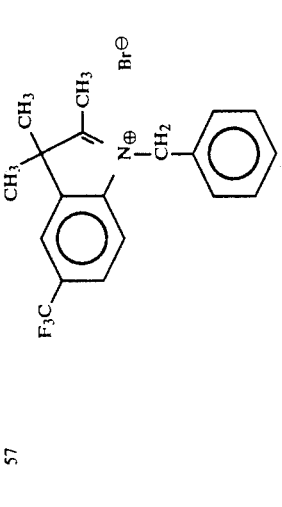 |  | 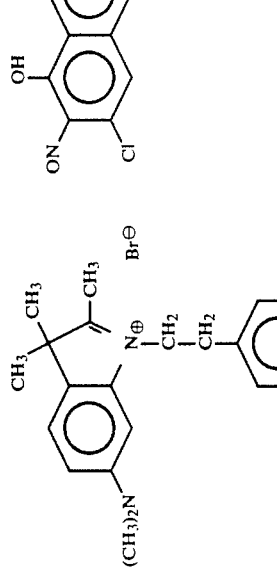 | | 5 |

TABLE 7-continued

| Example No. | Starting Compounds | | Condensation Agent | Products | Yield (%) |
|---|---|---|---|---|---|
| 60 | (quaternary ammonium bromide with mesityl group) | (8-chloro-5-methoxy-6-hydroxy-2-nitronaphthalene/quinoline) | NaCO₃ | (condensation product) | 3 |
| 61 | (quaternary ammonium bromide with biphenyl group) | (4-chloro-8-hydroxy-5-cyano-2-nitro quinoline) | NaOH | (condensation product) | 4 |
| 62 | (quaternary ammonium bromide with pyridyl group) | (8-bromo-5-hydroxy-7-trifluoromethyl-2-nitroquinoline) | pyrrolidine (NH) | (condensation product) | 2 |

TABLE 7-continued

| Example No. | Starting Compounds | Condensation Agent | Products | Yield (%) |
|---|---|---|---|---|
| 63 | (structures) | piperidine | (structures) | 3 |
| 64 | (structures) | piperidine | (structures) | 4 |

TABLE 8

| Example No. | Elementary Analysis Value (%) | | | | | Theoretical Values (%) | | | | |
|---|---|---|---|---|---|---|---|---|---|---|
| | C | H | N | O | others | C | H | N | O | others |
| 54 | 68.95 | 4.72 | 11.42 | 4.40 | F: 10.51 | 69.03 | 4.69 | 11.50 | 4.38 | F: 10.40 |
| 55 | 70.92 | 6.03 | 10.25 | 4.01 | Cl: 8.79 | 71.01 | 5.96 | 10.35 | 3.94 | Cl: 8.73 |
| 56 | 64.53 | 5.68 | 8.93 | 3.51 | Br: 17.35 | 64.66 | 5.64 | 9.05 | 3.45 | Br: 17.21 |
| 57 | 74.77 | 5.30 | 7.15 | 2.78 | F: 10.60 | 74.85 | 5.23 | 7.27 | 2.77 | F: 9.87 |
| 58 | 77.53 | 5.85 | 7.69 | 8.93 | — | 77.61 | 5.77 | 7.76 | 8.86 | — |
| 59 | 70.62 | 6.04 | 10.59 | 5.96 | Cl: 6.79 | 70.64 | 5.93 | 10.63 | 6.07 | Cl: 6.73 |
| 60 | 65.00 | 5.52 | 8.68 | 13.30 | Cl: 7.50 | 65.06 | 5.46 | 8.75 | 13.33 | Cl: 7.39 |
| 61 | 68.81 | 4.50 | 10.70 | 9.10 | Cl: 6.89 | 68.90 | 4.43 | 10.71 | 9.18 | Cl: 6.78 |
| 62 | 52.45 | 3.73 | 10.12 | 8.63 | Br: 14.62 F: 10.45 | 52.47 | 3.67 | 10.20 | 8.74 | Br: 14.55 F: 10.38 |
| 63 | 66.52 | 5.24 | 17.87 | 3.44 | S: 6.93 | 66.65 | 5.16 | 17.94 | 3.41 | S: 6.84 |
| 64 | 71.60 | 5.75 | 13.41 | 9.24 | — | 71.66 | 5.63 | 13.48 | 9.24 | — |

EXAMPLES 65 TO 128 AND COMPARATIVE EXAMPLES 1 AND 2

The compound synthesized in Example 1, which was represented by the following formula:

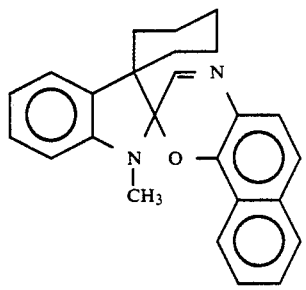

was dissolved and dispersed in polymethyl methacrylate with the aid of benzene, and a cast film was prepared on a slide glass sheet (11.2 cm × 3.7 cm) so that the concentration of the compound in the film was $1.0 \times 10^{-4}$ mol/g and the thickness of the film was 0.1 mm. The photochromic film was irradiated with rays of a mercury lamp (SHL-100 supplied by Toshiba) located 10 cm apart from the film at 35° C. +1° C. for 60 seconds to effect coloration in the film, and the photochromic characteristics were examined with respect to items described below. The obtained results of Example 65 are shown in Table 9.

Maximum absorption wavelength (λmax):

The maximum absorption wavelength λmax of the colored film was determined by using a spectrophotometer (220 A supplied by Hitachi).

ε(60 seconds):

After 60 seconds' irradiation under the above-mentioned conditions, the absorbance at the maximum absorption wavelength was measured.

ε(0 second):

The absorbance at the maximum absorption wavelength of the unirradiated film was measured. Half-value period $t_{\frac{1}{2}}$:

After 60 seconds' irradiation, the time required for reduction of the absorbance of the film to ½ of [ε(60 seconds)−ε(0 second)] was measured.

The photochromic characteristics of the films which were prepared in Examples 66 to 128 by using the spiroxazine compounds synthesized in Examples 2 to 64, respectively were measured in the same method as described in Example 65. The obtained results of Examples 66 to 128 are shown in Table 9.

For comparison, films were prepared by using known spiroxazines represented by the following formulae (65 and (66):

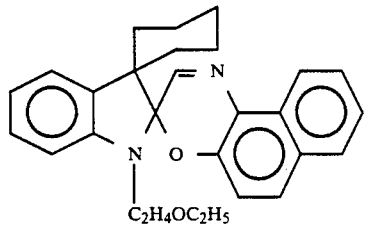

(65)

and

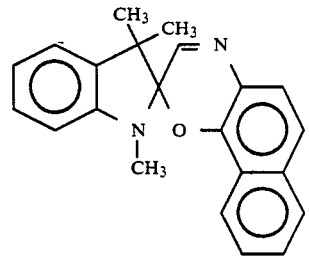

(66)

The photochromatic characteristics were similarly measured in the same method as Example 65. The results of comparative Examples 1 and 2 are shown in Table 9.

TABLE 9

| Example No. | Compounds | ε (60 seconds)− ε (0 second) | λ max | $t_{\frac{1}{2}}$ |
|---|---|---|---|---|
| 65 | 1 | 1.4 | 601 | 18 |
| 66 | 2 | 1.4 | 603 | 18 |
| 67 | 3 | 1.3 | 603 | 18 |
| 68 | 4 | 1.4 | 605 | 18 |
| 69 | 5 | 1.7 | 598 | 16 |
| 70 | 6 | 1.3 | 606 | 18 |
| 71 | 7 | 1.8 | 601 | 18 |
| 72 | 8 | 1.4 | 603 | 18 |
| 73 | 9 | 1.2 | 605 | 17 |
| 74 | 10 | 1.3 | 603 | 16 |
| 75 | 11 | 1.3 | 607 | 17 |
| 76 | 12 | 1.3 | 607 | 18 |
| 77 | 13 | 1.4 | 607 | 18 |
| 78 | 14 | 1.4 | 606 | 16 |
| 79 | 15 | 1.3 | 607 | 16 |
| 80 | 16 | 1.2 | 606 | 17 |
| 81 | 17 | 1.4 | 606 | 18 |
| 82 | 18 | 1.2 | 607 | 18 |
| 83 | 19 | 1.2 | 607 | 17 |
| 84 | 20 | 1.4 | 603 | 17 |
| 85 | 21 | 1.2 | 610 | 18 |
| 86 | 22 | 1.3 | 600 | 18 |
| 87 | 23 | 1.2 | 605 | 19 |

TABLE 9-continued

| Example No. | Compounds | ε (60 seconds)–ε (0 second) | λ max | t½ |
|---|---|---|---|---|
| 88 | 24 | 1.2 | 609 | 18 |
| 89 | 25 | 1.4 | 611 | 18 |
| 90 | 26 | 1.8 | 619 | 17 |
| 91 | 27 | 1.7 | 613 | 15 |
| 92 | 28 | 1.7 | 595 | 14 |
| 93 | 29 | 1.6 | 602 | 16 |
| 94 | 30 | 1.6 | 589 | 18 |
| 95 | 31 | 1.7 | 619 | 17 |
| 96 | 32 | 1.7 | 590 | 19 |
| 97 | 33 | 1.4 | 601 | 17 |
| 98 | 34 | 1.5 | 584 | 18 |
| 99 | 35 | 1.4 | 605 | 16 |
| 100 | 36 | 1.4 | 592 | 15 |
| 101 | 37 | 1.4 | 607 | 19 |
| 102 | 38 | 1.5 | 600 | 17 |
| 103 | 39 | 1.4 | 601 | 18 |
| 104 | 40 | 0.9 | 597 | 16 |
| 105 | 41 | 1.3 | 601 | 16 |
| 106 | 42 | 1.4 | 600 | 16 |
| 107 | 43 | 1.4 | 598 | 17 |
| 108 | 44 | 1.4 | 595 | 15 |
| 109 | 45 | 1.3 | 602 | 16 |
| 110 | 46 | 1.4 | 600 | 16 |
| 111 | 47 | 1.4 | 601 | 17 |
| 112 | 48 | 1.4 | 610 | 18 |
| 113 | 47 | 1.5 | 600 | 19 |
| 114 | 48 | 1.5 | 605 | 18 |
| 115 | 49 | 1.4 | 609 | 18 |
| 116 | 50 | 1.5 | 611 | 18 |
| 117 | 51 | 1.7 | 615 | 16 |
| 118 | 52 | 1.5 | 609 | 14 |
| 119 | 53 | 1.6 | 590 | 13 |
| 120 | 56 | 1.4 | 598 | 15 |
| 121 | 57 | 1.5 | 584 | 16 |
| 122 | 58 | 1.5 | 615 | 16 |
| 123 | 59 | 1.6 | 585 | 18 |
| 124 | 60 | 1.5 | 596 | 16 |
| 125 | 61 | 1.6 | 579 | 17 |
| 126 | 62 | 1.5 | 600 | 15 |
| 127 | 63 | 1.4 | 587 | 14 |
| 128 | 64 | 1.4 | 602 | 18 |
| Comparative Example 1 | 65 | 0.2 | 600 | 5 |
| Comparative Example 2 | 66 | 0.4 | 594 | 9 |

EXAMPLE 129

0.4 parts by weight of the spiroxazine synthesized in Example 1 was added to a composition of 70 parts by weight of chlorostyrene with 30 parts by weight of 2,2-bis(3,5-dibromo-4-methacryloyloxyethoxyphenyl)propane. One part by weight of perbutyl ND was added to the composition as an initiator of radical polymerization and was sufficiently mixed. The mixture liquid was casted into a mold comprising a glass plate and a gasket made of an ethylene-vinyl acetate copolymer and was polymerized in the mold. The mold was placed in an air oven. Polymerization was carried out by gradually elevating the temperature of the air oven from 30° C. to 90° C. for 18 hours and keeping it at 90° C. over a period of 2 hours. After the termination of the polymerization, the mold was removed from the air oven. After the mold was allowed to cool, the polymer molded piece was removed from the glass of the mold.

The photochromic characteristics of the obtained molded piece having a thickness of 2 mm was measured in the same method as Example 65. The results of Example 129 was shown in Table 10.

EXAMPLES 130 TO 144

Excepting that the kinds and amounts of the monomers and the spiroxazine used in Example 129 were changed and polymerization was carried out by a known means depending on the monomers, Examples 130 to 144 are identical with Example 129. The results are shown in Table 10.

The abbreviations in Table 10 represent the following compounds.

BMDBP: 2,2-bis(4-methacryloyloxyethoxy-3,5-dibromophenyl)propane,
Cl-St: chlorostyrene,
TMP-TAC: trimethylolpropane triallyl carbonate,
BADBD 2,2-bis(4-allyl carbonate ethoxy-3,5-dibromophenyl)propane,
ADC: allyl diglycol carbonate,
DAP: diallyl phthalate,
St: styrene,
DCIPF: di(2-chloroisopropyl) fumarate,
EGDMA: ethylene glycol dimethacrylate,
PETTP: pertaerythritoltetrakis (β-thiopropionate),
DME: di(2-mercaptoethyl)ether,
DVB: divinyl benzene,
XIC: xylylene diisocyanate,
HPA: 3-(2,4-dibromophenoxy)-2-hydroxypropyl acrylate,
MMA: methyl methacrylate,
DEGDMA: diethylene glycol dimethacrylate,
TBBM: 3,4,5-tribromobenzyl methacrylate,
HEMA: 2-hydroxyethyl methacrylate,
BMA: benzyl methacrylate,
IPP: diisopropylperoxy carbonate,
perbutyl ND: (Tradename: manufactured by Nippon Yushi K.K.) t-butylperoxy-2-hexanate

TABLE 10

| Example No. | Monomer composition of thermo-setting resin | No (parts by weight) of the compound represented by the general formula [I] | Initiator | ε(60 sec)–ε(0 sec) | λmax (nm) | t½ (sec) |
|---|---|---|---|---|---|---|
| 129 | BMDBP/cl-st (30/70) | 1(0.4) | perbutyl ND (1.0) | 1.6 | 604 | 20 |
| 130 | ADC (100) | 1(0.001) | IPP (3.0) | 0.9 | 607 | 24 |
| 131 | TMP-TAC(100) | 1(0.4) | IPP (2.0) | 1.5 | 607 | 28 |
| 132 | BADBP/DAP (60/40) | 1(0.4) | IPP (3.0) | 1.5 | 606 | 21 |
| 133 | BMDBP/st (50/50) | 1(10) | perbutyl ND (1.0) | 1.7 | 604 | 20 |
| 134 | DCIPF/st (70/30) | 1(70) | perbutyl ND (2.0) | 1.8 | 604 | 18 |
| 135 | EGDMA/st (50/50) | 1(30) | perbutyl ND (1.0) | 1.7 | 604 | 19 |

TABLE 10-continued

| Example No. | Monomer composition of thermo-setting resin | No (parts by weight) of the compound represented by the general formula [I] | Initiator | ε(60 sec)−ε(0 sec) | λmax (nm) | t½ (sec) |
|---|---|---|---|---|---|---|
| 136 | $CH_2=CHCSC_2H_4SC_2H_5$ (with C=O) /BMDBP (50/50) | 1(1.0) | perbutyl ND (1.0) | 1.6 | 601 | 20 |
| 137 | $CH_2=CCSC_2H_4SCC=CH_2$ with $CH_3$ groups and two C=O (100) | 1(0.6) | perbutyl ND (1.0) | 1.6 | 601 | 22 |
| 138 | DVB/PETTP(60/40) | 1(0.03) | IPP (0.5) | 1.5 | 606 | 22 |
| 139 | XIC/DME (58/42) | 1(0.2) | — | 1.5 | 604 | 19 |
| 140 | XIC/HPA/DVB (10/50/40) | 1(0.4) | dibutyltin-dilaurate (0.01) | 1.6 | 604 | 19 |
| 141 | MMA/DEGDMA (70/30) | 1(0.1) | perbutyl ND (1.0) | 1.6 | 601 | 18 |
| 142 | BADBPO/TBBM/DAP (50/30/20) | 1(0.1) | IPP(3.0) | 1.6 | 606 | 23 |
| 143 | HEMA/XIC/BMA (30/20/50) | 1(0.1) | perbutyl ND (1.0) | 1.6 | 601 | 22 |
| 144 | DEGDMA/BMA (40/60) | 1(0.1) | perbutyl ND (1.0) | 1.6 | 601 | 19 |

We claim:
1. A spiroxazine compound represented by the following general formula (I)

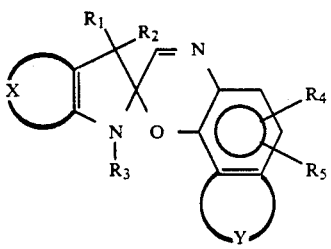

where $R_1$ and $R_2$ may be the same or different alkyl groups having 1 to 20 carbon atoms, or may together form a cycloalkyl ring, a bicycloalkyl ring or a tricycloalkyl ring, $R_3$ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms, $R_4$ and $R_5$, which may be the same or different, represent a hydrogen atom, a halogen atom, an alkyl group having 1 to 10 carbon atoms, an aryl group having 6 to 10 carbon atoms, an alkoxy group having 1 to 10 carbon atoms, a cyano group, a halogenoalkyl group having 1 to 4 carbon atoms, an amino group, a dialkylamino group having 2 to 20 carbon atoms, a 5- or 6-membered monocyclic heterocyclic group having one nitrogen atom or an alkoxycarbonyl group having 1 to 5 carbon atoms,

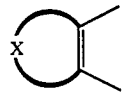

represents a group selected from the group consisting of an aromatic hydrocarbon group, a 5- or 6-membered unsaturated heterocyclic group containing oxygen, sulfur or nitrogen atoms and said unsaturated heterocyclic group fused to a benzene ring, which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenalkyl group having 1 to 4 carbon atoms, a 5- or 6-membered monocyclic heterocyclic group, an aralkyl group having 7 to 14 carbon atoms or an alkoxycarbonyl group having 1 to 5 carbon atoms, and

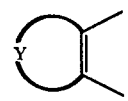

represents a group selected from the group consisting of an aromatic hydrocarbon group, a 5- or 6-membered unsaturated heterocyclic group containing oxygen, sulfur or nitrogen atoms and said unsaturated heterocyclic group fused to a benzene ring, which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms, with the proviso that when $R_1$ and $R_2$ are both methyl group, said aromatic hydrocarbon group is a fused polycyclic aromatic hydrocarbon group.

2. A spiroxazine compound represented by the following general formula (II)

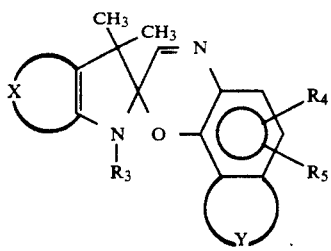

R₃ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms, R₄ and R₅, which may be the same or different, represent a hydrogen atom, a halogen atom, an alkyl group having 1 to 10 carbon atoms, an aryl group having 6 to 10 carbon atoms, an aralkyl group having 7 to 14 carbon atoms, an alkoxy group having 1 to 10 carbon atoms, a cyano group, a halogenoalkyl group having 1 to 4 carbon atoms, an amino group, a dialkylamino group having 2 to 20 carbon atoms, a 5- or 6-membered monocyclic heterocyclic group having 1 to 5 carbon atoms,

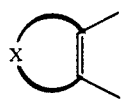

represents a group selected from the group consisting of an aromatic hydrocarbon group, a 5- or 6-membered unsaturated heterocyclic group containing oxygen, sulfur or nitrogen atoms and said unsaturated heterocyclic group fused to a benzene ring, which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenalkyl group having 1 to 4 carbon atoms, a 5- or 6-membered monocyclic heterocyclic group, an aralkyl group having 7 to 14 carbon atoms or an alkoxycarbonyl group having 1 to 5 carbon atoms, and

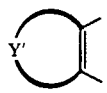

represents a group selected from the group consisting of a fused polycyclic aromatic hydrocarbon group, a 5-or 6-membered unsaturated heterocyclic group containing oxygen, sulfur or nitrogen atoms and said unsaturated heterocyclic group fused to a benzene ring, which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms.

3. A spiroxazine compound represented by the following general formula (III)

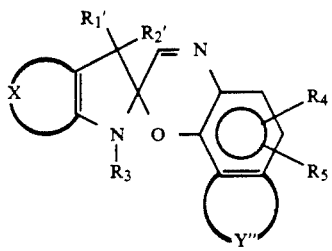

wherein $R_1'$ and $R_2'$ may be the same or different alkyl groups having 1 to 20 carbon atoms, or may together form a cycloalkyl ring, a bicycloalkyl ring or a tricycloalkyl ring, with the proviso that when $R_1'$ and $R_2'$ are both alkyl groups, at least one is an alkyl group having more than one carbon atom, R₃ represents an alkyl group having 1 to 10 carbon atoms, an aryl group having 6 to 10 carbon atoms, an aralkyl group having 7 to 14 carbon atoms, an alkoxycarbonylalkyl group including an alkoxy group having 1 to 10 carbon atoms and an alkylene group having 1 to 10 carbon atoms or a cyanoalkyl group having 1 to 10 carbon atoms, R₄ and R₅, which may be the same or different, represent a hydrogen atom, a halogen atom, an alkyl group having 1 to 10 carbon atoms, an aryl group having 6 to 10 carbon atoms, an aralkyl group having 7 to 14 carbon atoms, an alkoxy group having 1 to 10 carbon atoms, a cyano group, a halogenoalkyl group having 1 to 4 carbon atoms, an amino group, a dialkylamino group having 2 to 20 carbon atoms, a 5- or 6-membered monocyclic heterocyclic group having one nitrogen atom or an alkoxycarbonyl group having 1 to 5 carbon atoms,

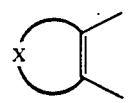

represents a group selected from the group consisting of an aromatic hydrocarbon group, a 5- or 6-membered unsaturated heterocyclic group containing oxygen, sulfur or nitrogen atoms and said unsaturated heterocyclic group fused to a benzene ring, which may be substituted with a halogen atom, a hydroxyl group, a cyano group, a nitro group, an alkyl group having 1 to 20 carbon atoms, an alkoxy group having 1 to 20 carbon atoms, an aryl group having 6 to 10 carbon atoms, an alkylamino group having 1 to 4 carbon atoms, a dialkylamino group having 2 to 8 carbon atoms, a halogenalkyl group having 1 to 4 carbon atoms, a 5- or 6-membered monocyclic heterocyclic group, an aralkyl group having 7 to 14 carbon atoms or an alkoxycarbonyl group having 1 to 5 carbon atoms, and

represents a group selected from the group consisting of an aromatic hydrocarbon group, a 5- or 6-membered unsaturated heterocyclic group containing oxygen, sulfur or nitrogen atoms and said unsaturated heterocyclic group fused to a benzene ring, which may be substituted with a halogen atom, a cyano group, a nitro group, an alkyl group having 1 to 20 carbon atoms, an alkoxy group having 1 to 20 carbon atoms, an amino group or a dialkylamino group having 2 to 8 carbon atoms.

4. A spiroxazine compound as set forth in claims 1, 2 or 3 wherein at least one of

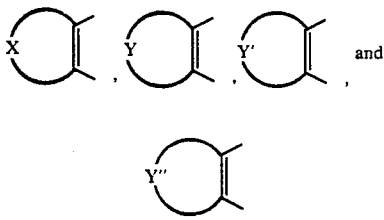

represent the aromatic hydrocarbon group which is a divalent group having 6 to 18 carbon atoms derived from one benzene ring or fused ring comprising 2 to 4 benzene rings.

5. A spiroxazine compound as set forth in claims 1, 2 or 3 wherein at least one of

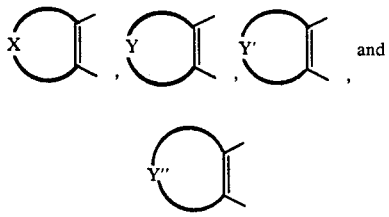

represent the unsaturated heterocyclic group which is a divalent group derived from a 5- or 6-membered heterocyclic ring containing oxygen, sulfur or nitrogen atoms or a fused heterocyclic ring formed by fusion of a benzene ring to the 5- or 6-membered heterocyclic ring.

6. A spiroxazine compound as set forth in claims 1, 2 or 3 wherein the aromatic hydrocarbon group represented by

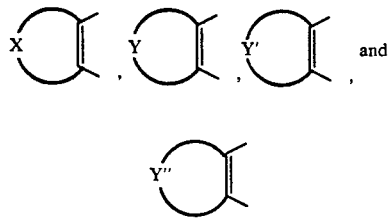

is a divalent group derived from a benzene ring or a naphthalene ring.

7. A spiroxazine compound as set forth in claims 1, 2 or 3 wherein the unsaturated heterocyclic group represented by

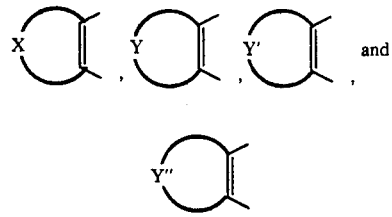

is a divalent group derived from a pyridine ring, a quinoline ring, a pyrrole ring, an indole ring, a furan ring, a benzofuran ring, a thiophene ring or a benzothiophene ring.

8. A spiroxazine compound as set forth in claim 2 wherein the unsaturated heterocyclic group represented by

is a divalent group derived from a pyridine ring, a quinoline ring, a pyrrole ring, an indole ring, a furan ring, a benzofuran ring, a thiophene ring or a benzothiophene ring.

9. A spiroxazine compound as set forth in claim 3 wherein the unsaturated heterocyclic group represented by

is a divalent group derived from a pyridine ring, a quinoline ring, a pyrrole ring, an indole ring, a furan ring, a benzofuran ring, a thiophene ring or a benzothiophene ring.

10. A spiroxazine compound as set forth in claim 8 or claim 9 wherein the divalent group is derived from a pyridine ring represented by the formula:

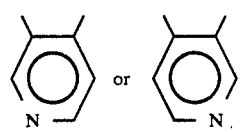

11. A spiroxazine compound as set forth in claim 8 or claim 9 wherein the divalent group is derived from a pyridine ring represented by the formula:

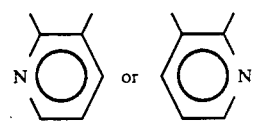

12. A spiroxazine compound as set forth in claim 1 or claim 2 wherein the fused polycyclic aromatic hydrocarbon group is a divalent group derived from a naphthalene group.

13. A photochromic polymeric composition comprising a polymeric matrix and dispersed therein a spiroxazine compound of general formula (I) as set forth in claim 1.

14. The composition of claim 13 which comprises from 0.001 to 70 parts by weight of the compound of general formula (I) per 100 parts by weight of the polymer.

15. The composition of claim 13 wherein the polymeric matrix comprises a thermoplastic polymer.

16. The composition of claim 13 wherein the polymeric matrix comprises a thermosetting resin.

17. A photochromic lens formed from the composition of claim 13 or claim 14.

18. A spiroxazine compound as set forth in claim 8 wherein the unsaturated heterocyclic group represented by

is a divalent group derived from a pyridine ring, a quinoline ring, a pyrrole ring, an indole ring, a furan ring, a benzofuran ring, a thiophene ring or a benzothiophene ring.

19. A spiroxazine compound as set forth in claim 9 wherein the unsaturated heterocyclic group represented by

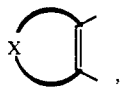

is a divalent group derived from a pyridine ring, a quinoline ring, a pyrrole ring, an indole ring, a furan ring, a benzofuran ring, a thiophene ring or a benzothiophene ring.

20. A spiroxazine compound as set forth in claim 7 wherein the aromatic carbon group represented by

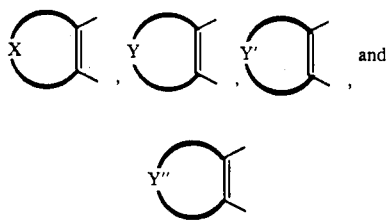

is a divalent group having 6 to 18 carbon atoms derived from one benzene ring or fused ring comprising 2 to 4 benzene rings.

21. A spiroxazine compound of general formula (I) as set forth in claim 1 which is selected from the group consisting of (1) 5'-fluoro-1'-methyldispiro[cyclohexane-1,3'-[3H]indole-2'(1'H),2''-[2H]naphth[1,2-b][1,4]oxazine]

(2) 5'-chloro-1'-methyldispiro[cyclopentane-1,3'-[3H]indole-2'(1'H),2''-[2H]naphth[1,2-b][1,4]oxazine]

(3) 5',7'-difluoro-1'-methyldispiro[cyclopentane-1,3'-[3H]indole-2'(1'H),2''-[2H]naphth[1,2-b][1,4]oxazine]

(4) 4'-methoxy-1'-methyldispiro[cyclopentane-1,3'-[3H]indole-2'(1'H),2''-[2H]naphth[1,2-b][1,4]oxazine]

(5) 1'-methyldispiro[cyclopentane-1,3'-[3H]indole-2'(1'H),2''-[2H]naphth[1,2-b][1,4]oxazine]

(6) 6'-dimethylamino-1'-methyldispiro[norbornane-2,3'[3H]indole-2'(1'H),2''-[2H]naphth[1,2-b][1,4]oxazine]

(7) 1'-propyl-5'-trifluoromethyldispiro[tricyclo[3.3.1.1$^{3,7}$]decane-2,3'-[3H]indole-2'(1'H),2''-[2H]naphth [1,2-b][1,4]oxazine]

(8) 5'-dimethylamino-6''-bromo-1'-methylcarbonylmethyldispiro[cycloheptane-1,3'-[3H]indole-2'(1'H),2''-[2H]naphth[1,2-b][1,4]oxazine]

(9) 5'-methoxy-1'-phenyldispiro[cyclopentane-1,3'-[3H]indole-2'(1'H),2''-[2H]naphth[1,2-b][1,4]oxazine]

(10) 1'-methyl-5'-nitrodispiro[cyclopentane-1,3'-[3H]indole-2'(1'H),2''-[2H]naphth[1,2-b][1,4]oxazine]

(11) 6'-benzyl-1'-methyldispiro[cyclopentane-1,3'-[3H]indole-2'(1'H),2''-[2H]naphth[1,2-b][1,4]oxazine]

(12) 1,3-dihydro-1,3,3-trimethyldispiro[2H-indole-2,2'-[2H]pyrido[2,3-h][1,4]benzoxazine]

(13) 9''-cyano-1'-(2-phenylethyl)dispiro[cyclohexane-1,2'-[3H]indole-2'(1'H),2H]pyrido[2,3-h][1,4]benzoxazine]

(14) 5'chloro-1'-methyl-6''-piperidinodispiro [tricyclo[3.3.1.1$^{3,7}$]decane-2,3'-[3H]indole-2'(1'H),2''-[2H]pyrido[2,3-h][1,4]benzoxazine]

(15) 1'-methoxycarbonxylmethyl-6''-phenyldispiro [norbornane-2,3'-[3H]indole-2'(1'H),2''-[2H]pyrido[2,3-h][1,4]benzoxazine]

(16) 1,3-dihydro-5'-trifluoromethyl-1,3,3-trimethyldispiro[2H-indole-2,2'-[2H]pyrido[2,3-h][1,4]benzoxazine]

(17) 1-cyanomethyl-1,3-dihydro-3,3-dimethyl-5-trifluoromethylspiro[2H-indole-2,2'-[2H]pyrido[2,3-h][1,4]benzoxazine]

(18) 1,3-dihydro-3,3-dimethyl-1-ethyl-6'3-phenylspiro [2H-indole-2,2'-[2H]pyrido[2,3-h][1,4]benzoxazine]

(19) 1,3-dihydro-6'-pyrrolidino-1,3,3-trimethylspiro [2H-indole-2,2'-[2H]pyrido[2,3-h][1,4]benzoxazine]

(20) 6'-benzyl-9'-bromo-5-cyano-1,3,3-trimethylspiro[2H-indole-2,2'-[2H]pyrido[2,3-h][1,4]benzoxazine]

(21) 1,3-dihydro-6-pyrrolidino-5'-trifluoromethyl-1,3,3-trimethylspiro[2H-indole-2,2'-[2H]pyrido[2,3-h][1,4]benzoxazine]

(22) 5'-amino-1,3-dihydro-1,3,3-trimethylspiro[2H-indole-2,2'-[2H]pyrido[2,3-h][1,4]benzoxazine]

(23) 1,3-dihydro-5'-methoxycarbonyl-1,3,3-trimethyl-5,6,7-tri(trifluoromethyl)spiro[2H-indole-2,2'-[2H]pyrido[2,3-h][1,4]benzoxazine]

(24) 1,3-dihydro-1,3,3-trimethylspiro[2H-indole-2,2'-[2H]pyrido[3,4-h][1,4]benzoxazine]

(25) 1,3-dihydro-1,3,3-trimethylspiro[2H-indole-2,2'[2H]pyrido[3,4-h][1,4]benzoxazine]

(26) 1,3-dihydro-5-fluoro-1,3,3-trimethylsprio[2H-indole-2,2'-[2H]pyrido[3,4-H][1,4]benzoxazine]

(27) 5-chloro-1,3-dihydro-1,3,3-trimethylspiro[2H-indole-2,2'-[2H]pyrido[3,4-h][1,4]benzoxazine]

(28) 7'-bromo-1'-isopropylidispiro[cyclohexane-1,3'-[3H]indole-2'(1'H),2''-[2H]pyrido[3,4-h][1,4]benoxazine]
(29) 1,3-dihydro-5-trifluormethyl-1,3,3-trimethylspiro[2H-indole-2,2'-[2H]pyrido[3,4-h][1,4]benzoxazine]
(30) 6'-dimethylamino-1'-ethyl-6''-methoxydispiro[cyclopentane-1,3'-[3H]indole-2'(1'H),2''-[2H]pyrido [3,4-h][1,4]benzoxazine]
(31) 1'-benzyl-6''-dimethylamino-5'-phenyldispiro[cyclopentane-1,3'-[3H]indole-2'(1'H),2''-[2H]pyrido [3,4-h][1,4]benzoxazine]
(32) 1-methoxycarbonylmethyl-6'-cyano-1,3-dihydro-3,3-dimethylspiro[2H-indole-2,2'-[2H]pyrido[3,4-h][1,4]benzoxazine]
(33) 5'-chloro-1-cyanomethyl-1,3-dihydro-3,3-dimethylspiro[2H-indole-2,2'-[2H]pyrido[3,4-h][1,4]benzoxazine
(34) 1,3-dihydro-3,3-dimethyl-1-(2-phenylethyl)-6'-pyrrolidinospiro[2H-indole-2,2'-[2H]-pyrido[3,4-h][1,4]benzoxazine]
(35) 1'-methyldispiro[norbornane-2-3'-[3H]indole-2'(1'H),2''-[2H]pyrido[3,4-h][1,4]benzoxazine]
(36) 1,3-dihydro-6'methoxycarbonyl-1,3,3-trimethylspiro[2H-indole-2,2'-[2H]pyrido[3,4-h][1,4]benzoxazine]
(37) 6-cyano-1,3-dihydro-1,3,3-trimethylspiro[2H-indole-2,2'-[2H]pyrido[4,3-h][1,4]benzoxazine]
(38) 1,3-dihydro-1,3,3-trimethylspiro[2H-indole-2,2'[2H]pyrido[4,3-h][1,4]benzoxazine]
(39) 1,3-dihydro-5-fluoro-1,3,3-trimethylspiro[2H-indole-2,2'[2H]pyrido[4,3-h][1,4]benzoxazine]
(40) 7-bromo-1,3-dihydro-1,3,3-triethylspiro[2H-indole-2,2'[2H]pyrido[4,3-h][1,4]benzoxazine]
(41) 1'-methyldispiro[cyclohexane-1,3'-[3H]indole-2'(1'H),2''-[2H]pyrido[4,3-h][1,4]benzoxazine]
(42) 1'-isopropyldispiro[cyclopentane-1,3'-[3H]indole-2'(1'H),2''-[2H]pyrido[4,3-h][1,4]benzoxazine]
(43) 1-benzyl-5-chloro-3,3-diethyl-1,3-dihydro-5'-methylspiro[2H-indole-2,2'-[2H]pyrido[4,3-h][1,4]benzoxazine]
(44) 5'-chloro-3,3-diethyl-1,3-dihydro-6-dimethylamino1-methylspiro[2H-indole-2,2'-[2H]pyrido [4,3-h][1,4]benzoxazine]
(45) 1,3-dihydro-3,3-dipropyl-8'-methoxy-1-methylspiro[2H-indole-2,2'-[2H]pyrido[4,3-h][1,4]benzoxazine]
(46) 6''-methoxy-1'-methyldispiro[norbornane-2,3-[3H]indole-2'(1'H),2''-[2H]pyrido[4,3-h][1,4 benzoxazine]
(47) 1-methoxycarbonylmethyl-1,3-dihydro-3,3-dimethylspiro[2H-indole-2,2'-[2H]pyrido[4,3-h][1,4]benzoxazine]
(48) 1-methoxycarbonylmethyl-6'cyano-1,3-dihydro-3,3-dimethyl-5-phenylspiro[2H-indole-2,2'-[2H]pyrido [4,3-h][1,4]benzoxazine]
(49) 7'-amino-1-cyanomethyl-1,3-dihydro-5-diethylamino-3ethyl-3-methylspiro[2H-indole-2,2'-[2H]pyrido[4,3-h][1,4]benzoxazine]
(50) 1'-methyl-6''-pyrrolidinodispiro[cyclohexane-1,3'-[3H]indole-2'(1'H),2''-[2H]pyrido[4,3-h][1,4]benzoxazine]
(51) 1-benzyl-5'-chloro-1,3-dihydro-3,3-dimethyl-6'-dimethylamino-8'-methoxyspiro[2H-indole-2,2'[2H]pyrido [4,3-h][1,4]benzoxazine]
(52) 1,3-dihydro-6'methoxycarbonyl-1,3,3-trimethylspiro[2H-indole-2,2'-[2H]pyrido[4,3-h][1,4]benzoxazine]
(53) 1,3-dihydro-1,3,3-trimethylspiro[2H-indole-2,2'-[2H]pyrido[3,2-h][1,4]benzoxazine]
(54) 1,3-dihydro-1,3,3-tripropylspiro[2H-indole-2,2'[2H]pyrido[3,2-h][1,4]benzoxazine]
(55) 1,3-dihydro-5-fluoro-1,3,3-trimpropylspiro[2H-indole-2,2'-[2H]pyrido[3,2-h][1,4]benzoxazine]
(56) 5chloro-1,3-dihydro-1,3,3-tripropylspiro[2H-indole-2,2'-[2H]pyrido[3,2-h][1,4]benzoxazine]
(57) 7'-bromo-1'-t-butyldispiro[cyclohexane-1,3-[3H]indole-2'(1'H),2''-[2H]pyrido[3,2-h][1,4]benzoxazine]
(58) 1,3-dihydro-5-trifluoromethyl-1,3,3-trimethylspiro[2H-indole-2,2'-[2H]pyrido[3,2-h][1,4]benzoxazine]
(59) 6'-dimethylamino-1'-ethyl-6''-methoxydispiro[cyclohexane-1,3'-[3H]indole-2'(1'H),2''-[2H]pyrido [3,2-h][1,4]benzoxazine]
(60) 1-benzyl-1,3-dihydro-3,3-dimethyl-6'-dimethylamino-5-phenylspiro[2H-indole-2,2'-[2H]pyrido [3,2-h][1,4]benoxazine]
(61) 1-methoxycarbonylmethyl-6'-cyano-1,3-dihydro-3,3-dimethylspiro[2H-indole-2,2'-[2H]pyrido[3,2-h][1,4]benzoxazine]
(62) 5'-chloro-1-(2-cyanoethyl)-1,3-dihydro-3,3-dimethylspiro[2H-indole-2,2'-[2H]pyrido[3,2-h][1,4]benzoxazine]
(63) 1,3-dihydro-3,3-dimethyl-6'-pyrrolidino-1-(2-phenylethyl)spiro[2H-indole-2,2'-[2H]pyrido[3,2-h][1,4]benzoxazine]
(64) 1'-methyldispiro[norbornane-2,3'-[3H]indole-2'(1'H),2''-[2H]pyrido[3,2-h][1,4]benoxazine]
(65) 1,3-dihydro-6'-ethoxycarbonyl-1,3,3-trimethylsprio[2H-indole-2,2'-[2H]pyrido[3,2-h][1,4]benzoxzine]
(66) 6-cyano-1,3-dihydro-1,3,3-trimethylspiro[2H-indole-2,2'-[2H]pyrido[3,2-h][1,4]benzoxazine]
(67) 1,3-dihydro-1,3,3-trimethylspiro[2H-indole-2,2'-[2H]anthara[1,2-b][1,4]oxazine]
(68) 1,3-dihydro-7'-methoxy-1,3,3-trimethylspiro[2H-indole-2,2'-[2H]anthara[1,2-b][1,4]oxazine]
(69) 1,3-dihydro-1,3,3-trimethylspiro[2H-indole-2,2'-[2H]([1H]pyrrolo)[6,7-b]naphth[1,3-b][1,4]oxazine]
(70) 1,3-dihydro-1,3,3-trimethylspiro[2H-indole-2,2'-[2H]([1H]pyrrolo)[2,3-b][1,4]benzoxazine]
(71) 1,3-dihydro-6-methoxycarbonyl-1,3,3-trimethylspiro[2H-indole-2,2'-[2H]([1H]pyrrolo)[2,3-h][1,4]benzoxazine]
(72) 1,3-dihydro-1,3,3-trimethylspiro[2H-indole-2,2'-[2H]thieno[2,3-h][1,4]benzoxazine]
(73) 1'-methyldispiro(cyclohexane-1,3'-[2H indole-2'(1H),2''-[2H]thieno[2,3-h][1,4]benzoxazine] and
(74) 1,3-dihydro-1,3,3-trimethylspiro[2H-indole-2,2'-[2H]furano[2,3-h][1,4]benzoxazine].

22. A spiroxazine compound as set forth in claim 1 wherein $R_3$ represents said alkyl group.
23. A spiroxazine compound as set forth in claim 1 wherein $R_3$ represents said aryl group.
24. A spiroxazine compound as set forth in claim 1 wherein $R_3$ represents said aralkyl group.
25. A spiroxazine compound as set forth in claim 1 wherein $R_3$ represents said alkoxycarbonylalkyl group.
26. A spiroxazine compound as set forth in claim 1 wherein $R_3$ represents said cyano alkyl group.

* * * * *